(12) United States Patent
McMillen

(10) Patent No.: US 10,282,011 B2
(45) Date of Patent: *May 7, 2019

(54) FLEXIBLE SENSORS AND APPLICATIONS

(71) Applicant: BeBop Sensors, Inc., Berkeley, CA (US)

(72) Inventor: Keith A. McMillen, Berkeley, CA (US)

(73) Assignee: BeBop Sensors, Inc., Berkeley, CA (US)

( * ) Notice: Subject to any disclaimer, the term of this patent is extended or adjusted under 35 U.S.C. 154(b) by 8 days.

This patent is subject to a terminal disclaimer.

(21) Appl. No.: 15/251,772

(22) Filed: Aug. 30, 2016

(65) Prior Publication Data
US 2017/0038881 A1   Feb. 9, 2017

Related U.S. Application Data

(60) Division of application No. 14/671,821, filed on Mar. 27, 2015, which is a continuation-in-part of application No. 14/299,976, filed on Jun. 9, 2014.
(Continued)

(51) Int. Cl.
*G01L 1/18* (2006.01)
*G01L 9/00* (2006.01)
(Continued)

(52) U.S. Cl.
CPC .......... *G06F 3/0414* (2013.01); *A61B 5/6843* (2013.01); *G01L 1/146* (2013.01);
(Continued)

(58) Field of Classification Search
CPC ... G01L 1/16; G01L 1/18; G01L 1/005; G01L 1/126; G01L 1/146; G01L 1/2287; G01L 1/205; G01L 9/0052; G01L 9/0002; G01L 9/06; G01L 9/0054; G01L 15/00; G01L 5/228; G01L 5/0052; G01L 17/005; G06F 3/0414; G06F 3/045; G06F 2203/04105; A61B 2562/0247; A61B 2562/227; A61B 2562/164; A61B 5/6843; A61B 5/6807; A61B 5/6806; A61B 5/6804; A61B 2090/064; A61B 2560/045; H03K 17/964;
(Continued)

(56) References Cited

U.S. PATENT DOCUMENTS

| 4,294,014 A | 10/1981 | Baumann et al. |
| 4,438,291 A | 3/1984 | Eichelberger et al. |

(Continued)

FOREIGN PATENT DOCUMENTS

| CN | 200980381 Y | 11/2007 |
| CN | 201920728 U | 8/2011 |

(Continued)

OTHER PUBLICATIONS

U.S. Appl. No. 15/052,293, Feb. 24, 2016, McMillen et al.
(Continued)

*Primary Examiner* — Dismery Mercedes
(74) *Attorney, Agent, or Firm* — Weaver Austin Villeneuve & Sampson LLP

(57) ABSTRACT

Sensors incorporating piezoresistive materials are described. One class of includes conductive traces formed directly on or otherwise integrated with the piezoresistive material.

19 Claims, 13 Drawing Sheets

Related U.S. Application Data

(60) Provisional application No. 61/993,953, filed on May 15, 2014, provisional application No. 62/057,130, filed on Sep. 29, 2014, provisional application No. 62/072,798, filed on Oct. 30, 2014, provisional application No. 61/993,953, filed on May 15, 2014.

(51) Int. Cl.
| | | |
|---|---|---|
| *H03K 17/96* | (2006.01) | |
| *G06F 3/041* | (2006.01) | |
| *G01L 15/00* | (2006.01) | |
| *G01L 1/14* | (2006.01) | |
| *G01L 17/00* | (2006.01) | |
| *A61B 5/00* | (2006.01) | |
| *G01L 1/20* | (2006.01) | |
| *G06F 1/16* | (2006.01) | |
| *G01L 1/26* | (2006.01) | |

(52) U.S. Cl.
CPC ............ *G01L 1/18* (2013.01); *G01L 1/205* (2013.01); *G01L 9/0052* (2013.01); *G01L 15/00* (2013.01); *G01L 17/005* (2013.01); *G06F 1/16* (2013.01); *G06F 3/0416* (2013.01); *H03K 17/964* (2013.01); *H03K 17/9643* (2013.01); *A61B 2562/0247* (2013.01); *A61B 2562/227* (2013.01); *G01L 1/26* (2013.01); *H03K 2017/9602* (2013.01); *H03K 2217/96019* (2013.01); *Y10T 29/49156* (2015.01)

(58) Field of Classification Search
CPC . H03K 2217/9651; H03K 2217/96019; H03K 2017/9602
See application file for complete search history.

(56) References Cited

U.S. PATENT DOCUMENTS

| | | | |
|---|---|---|---|
| 4,489,302 A | 12/1984 | Eventoff | |
| 4,693,530 A | 9/1987 | Stillie et al. | |
| 4,745,301 A * | 5/1988 | Michalchik | H01B 1/24 252/511 |
| 4,790,968 A | 12/1988 | Ohkawa et al. | |
| 4,852,443 A | 8/1989 | Duncan et al. | |
| 5,033,291 A | 7/1991 | Podoloff et al. | |
| 5,128,880 A | 7/1992 | White | |
| 5,131,306 A | 7/1992 | Yamamoto | |
| 5,159,159 A | 10/1992 | Asher | |
| 5,219,292 A | 6/1993 | Dickirson et al. | |
| 5,237,520 A | 8/1993 | White | |
| 5,288,938 A | 2/1994 | Wheaton | |
| 5,316,017 A | 5/1994 | Edwards et al. | |
| 5,386,720 A * | 2/1995 | Toda | B82Y 35/00 250/307 |
| 5,429,092 A | 7/1995 | Kamei | |
| 5,571,973 A | 11/1996 | Taylot | |
| 5,578,766 A | 11/1996 | Kondo | |
| 5,624,132 A | 4/1997 | Blackburn et al. | |
| 5,659,395 A | 8/1997 | Brown et al. | |
| 5,695,859 A | 12/1997 | Burgess | |
| 5,729,905 A | 3/1998 | Mathiasmeier et al. | |
| 5,822,223 A | 10/1998 | Genest | |
| 5,866,829 A | 2/1999 | Pecoraro | |
| 5,878,359 A | 3/1999 | Takeda | |
| 5,943,044 A | 8/1999 | Martinelli et al. | |
| 5,989,700 A | 11/1999 | Krivopal | |
| 6,029,358 A | 2/2000 | Mathiasmeier et al. | |
| 6,032,109 A | 2/2000 | Ritmiller, III | |
| 6,049,327 A | 4/2000 | Walker et al. | |
| 6,087,930 A | 7/2000 | Kulka et al. | |
| 6,121,869 A * | 9/2000 | Burgess | H01H 3/141 200/511 |
| 6,141,643 A | 10/2000 | Harmon | |
| 6,155,120 A | 12/2000 | Taylor | |
| 6,215,055 B1 | 4/2001 | Saravis | |
| 6,216,545 B1 | 4/2001 | Taylor | |
| 6,304,840 B1 | 10/2001 | Vance et al. | |
| 6,331,893 B1 | 12/2001 | Brown et al. | |
| 6,360,615 B1 * | 3/2002 | Smela | A61B 5/1124 73/862.474 |
| 6,452,479 B1 | 9/2002 | Sandbach | |
| 6,486,776 B1 | 11/2002 | Pollack et al. | |
| 6,687,523 B1 * | 2/2004 | Jayaramen | A41D 13/1281 600/388 |
| 6,763,320 B2 | 7/2004 | Kimble | |
| 6,815,602 B2 | 11/2004 | De Franco | |
| 6,822,635 B2 | 11/2004 | Shahoian et al. | |
| 6,829,942 B2 | 12/2004 | Yanai et al. | |
| 6,964,205 B2 | 11/2005 | Papakostas et al. | |
| 7,037,268 B1 * | 5/2006 | Sleva | B06B 1/0688 340/855.6 |
| 7,066,887 B2 | 6/2006 | Flesch et al. | |
| 7,109,068 B2 | 9/2006 | Akram et al. | |
| 7,113,856 B2 | 9/2006 | Theiss et al. | |
| 7,138,976 B1 | 11/2006 | Bouzit et al. | |
| 7,157,640 B2 | 1/2007 | Baggs | |
| 7,302,866 B1 | 12/2007 | Malkin et al. | |
| 7,311,009 B2 * | 12/2007 | Kotovsky | G01L 1/18 438/50 |
| 7,332,670 B2 | 2/2008 | Fujiwara et al. | |
| 7,409,256 B2 | 8/2008 | Lin et al. | |
| 7,439,465 B2 * | 10/2008 | Parkinson | H01H 13/78 200/512 |
| 7,493,230 B2 | 2/2009 | Schwartz et al. | |
| 7,536,794 B2 | 5/2009 | Hay et al. | |
| 7,584,666 B2 * | 9/2009 | Kim | A61B 5/021 128/897 |
| 7,608,776 B2 | 10/2009 | Ludwig | |
| 7,719,007 B2 * | 5/2010 | Tompkins | G01L 1/142 257/48 |
| 7,726,199 B2 * | 6/2010 | Shkel | G01L 1/142 73/780 |
| 7,754,956 B2 | 7/2010 | Gain et al. | |
| 7,780,541 B2 | 8/2010 | Bauer | |
| 7,855,718 B2 | 12/2010 | Westerman | |
| 7,928,312 B2 | 4/2011 | Sharma | |
| 7,984,544 B2 | 6/2011 | Rosenberg | |
| 8,109,149 B2 | 2/2012 | Kotovsky | |
| 8,117,922 B2 | 2/2012 | Xia et al. | |
| 8,120,232 B2 | 2/2012 | Daniel et al. | |
| 8,127,623 B2 | 3/2012 | Son et al. | |
| 8,161,826 B1 * | 4/2012 | Taylor | G01L 1/18 73/862.044 |
| 8,250,934 B2 * | 8/2012 | Sakurai | G01L 5/161 73/862.041 |
| 8,274,485 B2 | 9/2012 | Liu et al. | |
| 8,346,684 B2 | 1/2013 | Mirbach et al. | |
| 8,368,505 B2 * | 2/2013 | Deppiesse | H03K 17/965 338/114 |
| 8,448,530 B2 | 5/2013 | Leuenberger et al. | |
| 8,479,585 B2 | 7/2013 | Shaw-Klein | |
| 8,536,880 B2 | 9/2013 | Philipp | |
| 8,571,827 B2 | 10/2013 | Jang et al. | |
| 8,661,917 B2 * | 3/2014 | Jheng | H01B 1/24 73/862.68 |
| 8,680,390 B2 | 3/2014 | McMillen et al. | |
| 8,813,579 B2 * | 8/2014 | Aufrere | G01L 1/205 73/862.627 |
| 8,857,274 B2 | 10/2014 | Mamigonians | |
| 8,884,913 B2 | 11/2014 | Saynac et al. | |
| 8,892,051 B2 | 11/2014 | Yi et al. | |
| 8,893,565 B2 * | 11/2014 | White | G01L 1/14 73/862.626 |
| 8,904,876 B2 | 12/2014 | Taylor et al. | |
| 8,925,392 B2 * | 1/2015 | Esposito | A61B 5/1036 73/862.01 |
| 8,925,393 B2 | 1/2015 | Cannard et al. | |
| 8,928,014 B2 * | 1/2015 | Tischler | H01L 33/62 257/723 |
| 8,945,328 B2 | 2/2015 | Longinotti-Buitoni et al. | |

(56) References Cited

U.S. PATENT DOCUMENTS

| | | |
|---|---|---|
| 8,947,889 B2 | 2/2015 | Kelley et al. |
| 8,950,265 B2 | 2/2015 | Dunn et al. |
| 8,964,205 B2 | 2/2015 | Shimizu |
| 8,970,513 B2 | 3/2015 | Kwon et al. |
| 9,032,804 B2 * | 5/2015 | Granado ............... G01L 9/0052 73/700 |
| 9,038,482 B2 | 5/2015 | Xia et al. |
| 9,075,404 B2 | 7/2015 | McMillen et al. |
| 9,076,419 B2 | 7/2015 | McMillen et al. |
| 9,112,058 B2 | 8/2015 | Bao et al. |
| 9,116,569 B2 | 8/2015 | William et al. |
| 9,164,586 B2 | 10/2015 | Zellers et al. |
| 9,182,302 B2 * | 11/2015 | Lim .......................... G01L 1/18 |
| 9,271,665 B2 | 3/2016 | Sarrafzadeh et al. |
| 9,417,693 B2 | 8/2016 | Seth |
| 9,442,614 B2 | 9/2016 | McMillen |
| 9,480,582 B2 | 11/2016 | Lundborg |
| 9,529,433 B2 | 12/2016 | Shankar et al. |
| 9,546,921 B2 | 1/2017 | McMillen et al. |
| 9,652,101 B2 | 5/2017 | McMillen et al. |
| 9,682,856 B2 | 6/2017 | Whitesides et al. |
| 9,696,833 B2 * | 7/2017 | McMillen ............... G06F 1/163 |
| 9,710,060 B2 | 7/2017 | McMillen et al. |
| 9,721,553 B2 | 8/2017 | McMillen et al. |
| 9,753,568 B2 | 9/2017 | McMillen |
| 9,756,895 B2 * | 9/2017 | Rice .......................... G01L 1/20 |
| 9,827,996 B2 | 11/2017 | McMillen |
| 9,836,151 B2 | 12/2017 | McMillen |
| 9,863,823 B2 | 1/2018 | McMillen |
| 9,965,076 B2 | 5/2018 | McMillen |
| 10,082,381 B2 | 9/2018 | McMillen et al. |
| 10,114,493 B2 | 10/2018 | McMillen et al. |
| 2002/0078757 A1 | 6/2002 | Hines et al. |
| 2002/0180578 A1 * | 12/2002 | Sandbach ............... G06F 3/045 338/99 |
| 2004/0031180 A1 | 2/2004 | Ivanov |
| 2004/0093746 A1 | 5/2004 | Varsallona |
| 2004/0183648 A1 * | 9/2004 | Weber .................... G01L 5/0052 338/47 |
| 2004/0189145 A1 | 9/2004 | Pletner et al. |
| 2004/0252007 A1 | 12/2004 | Lussey et al. |
| 2005/0109095 A1 | 5/2005 | Sinnett |
| 2005/0220673 A1 | 10/2005 | Thaysen |
| 2007/0063992 A1 | 3/2007 | Lundquist |
| 2007/0129776 A1 | 6/2007 | Robins et al. |
| 2007/0151348 A1 | 7/2007 | Zdeblick et al. |
| 2007/0188179 A1 | 8/2007 | Deangelis et al. |
| 2007/0188180 A1 | 8/2007 | Deangelis et al. |
| 2007/0202765 A1 | 8/2007 | Krans et al. |
| 2007/0234888 A1 | 10/2007 | Rotolo de Moraes |
| 2008/0069412 A1 | 3/2008 | Champagne et al. |
| 2008/0158145 A1 | 7/2008 | Westerman |
| 2008/0189827 A1 | 8/2008 | Bauer |
| 2008/0254824 A1 | 10/2008 | Rotolo de Moraes |
| 2009/0013793 A1 * | 1/2009 | Kim ...................... A61B 5/021 73/727 |
| 2009/0049980 A1 | 2/2009 | Sharma |
| 2009/0134966 A1 * | 5/2009 | Baker ..................... G01L 1/20 338/99 |
| 2009/0237374 A1 | 9/2009 | Li et al. |
| 2009/0272197 A1 * | 11/2009 | Ridao Granado ........ G01L 1/20 73/828 |
| 2009/0301190 A1 | 12/2009 | Ross, Jr. et al. |
| 2009/0303400 A1 | 12/2009 | Hou et al. |
| 2010/0066572 A1 | 3/2010 | Dietz et al. |
| 2010/0123686 A1 | 5/2010 | Klinghult et al. |
| 2010/0134327 A1 | 6/2010 | Dinh et al. |
| 2010/0149108 A1 | 6/2010 | Hotelling et al. |
| 2010/0179724 A1 | 7/2010 | Weston |
| 2010/0199777 A1 | 8/2010 | Hooper et al. |
| 2010/0242274 A1 | 9/2010 | Rosenfeld et al. |
| 2010/0274447 A1 | 10/2010 | Stumpf |
| 2010/0286951 A1 | 11/2010 | Danenberg et al. |
| 2010/0292945 A1 | 11/2010 | Reynolds et al. |
| 2010/0315337 A1 | 12/2010 | Ferren et al. |
| 2011/0005090 A1 | 1/2011 | Lee et al. |
| 2011/0088535 A1 | 4/2011 | Zarimis |
| 2011/0088536 A1 * | 4/2011 | McMillen ............... G10H 1/348 84/746 |
| 2011/0107771 A1 | 5/2011 | Crist et al. |
| 2011/0141052 A1 | 6/2011 | Bernstein et al. |
| 2011/0153261 A1 | 6/2011 | Jang et al. |
| 2011/0199284 A1 | 8/2011 | Davis et al. |
| 2011/0221564 A1 * | 9/2011 | Deppiesse .......... H03K 17/9625 338/99 |
| 2011/0241850 A1 | 10/2011 | Bosch et al. |
| 2011/0246028 A1 | 10/2011 | Lisseman et al. |
| 2011/0260994 A1 | 10/2011 | Saynac et al. |
| 2011/0271772 A1 | 11/2011 | Parks et al. |
| 2011/0279409 A1 | 11/2011 | Salaverry et al. |
| 2011/0302694 A1 | 12/2011 | Wang et al. |
| 2012/0007831 A1 | 1/2012 | Chang et al. |
| 2012/0024132 A1 | 2/2012 | Wallace et al. |
| 2012/0026124 A1 | 2/2012 | Li et al. |
| 2012/0055257 A1 | 3/2012 | Shaw-Klein |
| 2012/0090408 A1 * | 4/2012 | Jheng ....................... G01L 1/18 73/862.68 |
| 2012/0143092 A1 | 6/2012 | Xia et al. |
| 2012/0191554 A1 | 7/2012 | Xia et al. |
| 2012/0197161 A1 | 8/2012 | Xia et al. |
| 2012/0198949 A1 | 8/2012 | Xia et al. |
| 2012/0222498 A1 | 9/2012 | Mamigonians |
| 2012/0234105 A1 | 9/2012 | Taylor |
| 2012/0283979 A1 | 11/2012 | Bruekers et al. |
| 2012/0296528 A1 | 11/2012 | Wellhoefer et al. |
| 2012/0297885 A1 | 11/2012 | Hou et al. |
| 2012/0299127 A1 | 11/2012 | Fujii et al. |
| 2012/0312102 A1 * | 12/2012 | alvarez ............... E21B 33/1208 73/862.041 |
| 2012/0323501 A1 | 12/2012 | Sarrafzadeh et al. |
| 2013/0009905 A1 | 1/2013 | Castillo et al. |
| 2013/0055482 A1 | 3/2013 | D'Aprile et al. |
| 2013/0082970 A1 | 4/2013 | Frey et al. |
| 2013/0085394 A1 | 4/2013 | Corbett, III et al. |
| 2013/0113057 A1 * | 5/2013 | Taylor ....................... G01L 1/18 257/417 |
| 2013/0113704 A1 | 5/2013 | Sarrafzadeh et al. |
| 2013/0165809 A1 | 6/2013 | Abir |
| 2013/0192071 A1 | 8/2013 | Esposito et al. |
| 2013/0203201 A1 | 8/2013 | Britton et al. |
| 2013/0211208 A1 | 8/2013 | Varadan et al. |
| 2013/0214365 A1 * | 8/2013 | Schlarmann .......... G01L 9/0042 257/415 |
| 2013/0239787 A1 | 9/2013 | McMillen et al. |
| 2013/0274985 A1 | 10/2013 | Lee et al. |
| 2013/0275057 A1 | 10/2013 | Perlin et al. |
| 2013/0327560 A1 | 12/2013 | Ichiki |
| 2013/0340598 A1 | 12/2013 | Marquez et al. |
| 2014/0007704 A1 * | 1/2014 | Granado ............... G01L 9/0052 73/862.627 |
| 2014/0007706 A1 * | 1/2014 | Aufrere .................... G01L 1/205 73/862.629 |
| 2014/0013865 A1 * | 1/2014 | White ....................... G01L 1/14 73/862.626 |
| 2014/0026678 A1 | 1/2014 | Cannard et al. |
| 2014/0033829 A1 | 2/2014 | Xia et al. |
| 2014/0090488 A1 | 4/2014 | Taylor et al. |
| 2014/0104776 A1 | 4/2014 | Clayton et al. |
| 2014/0104792 A1 * | 4/2014 | Jeziorek ............... H05K 3/0061 361/749 |
| 2014/0107966 A1 | 4/2014 | Xia et al. |
| 2014/0107967 A1 | 4/2014 | Xia et al. |
| 2014/0107968 A1 | 4/2014 | Xia et al. |
| 2014/0125124 A1 | 5/2014 | Verner |
| 2014/0130593 A1 | 5/2014 | Ciou et al. |
| 2014/0150573 A1 | 6/2014 | Cannard et al. |
| 2014/0182170 A1 | 7/2014 | Wawrousek et al. |
| 2014/0195023 A1 | 7/2014 | Statham et al. |
| 2014/0215684 A1 | 8/2014 | Hardy et al. |
| 2014/0222173 A1 | 8/2014 | Giedwoyn et al. |
| 2014/0222243 A1 | 8/2014 | McMillen et al. |

(56) References Cited

U.S. PATENT DOCUMENTS

| | | | |
|---|---|---|---|
| 2014/0264407 A1* | 9/2014 | Tischler | H01L 33/62 257/91 |
| 2014/0318699 A1* | 10/2014 | Longinotti-Buitoni | A61B 5/0002 156/247 |
| 2014/0347076 A1 | 11/2014 | Barton et al. | |
| 2015/0035743 A1 | 2/2015 | Rosener | |
| 2015/0084873 A1 | 3/2015 | Hagenbuch et al. | |
| 2015/0086955 A1 | 3/2015 | Poniatowski et al. | |
| 2015/0130698 A1 | 5/2015 | Burgess | |
| 2015/0168238 A1 | 6/2015 | Raut et al. | |
| 2015/0177080 A1 | 6/2015 | Esposito et al. | |
| 2015/0248159 A1 | 9/2015 | Luo et al. | |
| 2015/0261372 A1 | 9/2015 | McMillen et al. | |
| 2015/0316434 A1 | 11/2015 | McMillen et al. | |
| 2015/0317964 A1 | 11/2015 | McMillen et al. | |
| 2015/0330855 A1 | 11/2015 | Daniecki et al. | |
| 2015/0331512 A1 | 11/2015 | McMillen et al. | |
| 2015/0331522 A1 | 11/2015 | McMillen et al. | |
| 2015/0331523 A1 | 11/2015 | McMillen et al. | |
| 2015/0331524 A1 | 11/2015 | McMillen et al. | |
| 2015/0331533 A1 | 11/2015 | McMillen et al. | |
| 2015/0370396 A1 | 12/2015 | Hotelling et al. | |
| 2016/0052131 A1 | 2/2016 | Lessing et al. | |
| 2016/0054798 A1 | 2/2016 | Messingher et al. | |
| 2016/0070347 A1 | 3/2016 | McMillen et al. | |
| 2016/0073539 A1* | 3/2016 | Driscoll | H02M 7/219 361/750 |
| 2016/0147352 A1* | 5/2016 | Filiz | G01L 1/18 345/173 |
| 2016/0162022 A1 | 6/2016 | Seth | |
| 2016/0169754 A1 | 6/2016 | Kowalewski et al. | |
| 2016/0175186 A1 | 6/2016 | Shadduck | |
| 2016/0187973 A1 | 6/2016 | Shankar et al. | |
| 2016/0209441 A1 | 7/2016 | Mazzeo et al. | |
| 2016/0238547 A1 | 8/2016 | Park et al. | |
| 2016/0246369 A1 | 8/2016 | Osman | |
| 2016/0252412 A1 | 9/2016 | McMillen et al. | |
| 2016/0270727 A1 | 9/2016 | Berg et al. | |
| 2016/0278709 A1* | 9/2016 | Ridao Granado | A61B 5/0205 |
| 2016/0313798 A1 | 10/2016 | Connor | |
| 2016/0318356 A1 | 11/2016 | McMillen et al. | |
| 2016/0340534 A1* | 11/2016 | Wijesundara | C09D 11/52 |
| 2016/0375910 A1 | 12/2016 | McMillen et al. | |
| 2017/0000369 A1 | 1/2017 | Hyde et al. | |
| 2017/0056644 A1 | 3/2017 | Chahine et al. | |
| 2017/0086519 A1 | 3/2017 | Vigano et al. | |
| 2017/0108929 A1 | 4/2017 | Sinko et al. | |
| 2017/0110103 A1 | 4/2017 | McMillen et al. | |
| 2017/0127736 A1 | 5/2017 | Roberts et al. | |
| 2017/0167931 A1 | 6/2017 | McMillen et al. | |
| 2017/0212638 A1 | 7/2017 | McMillen | |
| 2017/0303853 A1 | 10/2017 | McMillen et al. | |
| 2017/0305301 A1 | 10/2017 | McMillen et al. | |
| 2018/0015932 A1 | 1/2018 | McMillen et al. | |
| 2018/0094991 A1 | 4/2018 | McMillen et al. | |
| 2018/0263563 A1 | 9/2018 | McMillen et al. | |

FOREIGN PATENT DOCUMENTS

| | | |
|---|---|---|
| CN | 102551728 A | 7/2012 |
| CN | 202396601 U | 8/2012 |
| CN | 203234132 U | 10/2013 |
| CN | 102406280 B | 3/2014 |
| DE | 102 12 023 A1 | 10/2003 |
| DE | 11 2010 004 038 T5 | 9/2012 |
| EP | 0 014 022 B1 | 11/1984 |
| EP | 0 211 984 | 3/1987 |
| EP | 2 682 724 A1 | 1/2014 |
| JP | S47-18925 | 5/1972 |
| JP | H04-011666 A | 1/1992 |
| JP | H06-323929 A | 11/1994 |
| JP | H08-194481 A | 7/1996 |
| JP | H10-198503 A | 7/1998 |
| JP | 2000-267664 A | 9/2000 |
| JP | 2007-503052 A | 2/2007 |
| JP | 2008-515008 A | 5/2008 |
| JP | 2009-543030 A | 12/2009 |
| JP | 2011-502313 A | 1/2011 |
| JP | 2012-521550 A | 9/2012 |
| JP | 2012-220315 A | 11/2012 |
| JP | 2014-077662 A | 5/2014 |
| KR | 10-2007-0008500 A | 1/2007 |
| KR | 100865148 B1 | 10/2008 |
| KR | 10-1362742 B1 | 2/2014 |
| KR | 10-2014-0071693 A | 6/2014 |
| NL | 8900820 A | 11/1990 |
| RU | 2 533 539 C1 | 11/2014 |
| WO | WO 99/020179 A1 | 4/1999 |
| WO | WO 2007/024875 A2 | 3/2007 |
| WO | WO 2008/032661 | 3/2008 |
| WO | WO 2009/155891 A1 | 12/2009 |
| WO | WO 2011/047171 A2 | 4/2011 |
| WO | WO 2013/181474 | 12/2013 |
| WO | WO 2015/175317 A1 | 11/2015 |
| WO | PCT/US16/19513 | 2/2016 |
| WO | PCT/US16/29528 | 4/2016 |
| WO | WO 2016/070078 A1 | 5/2016 |
| WO | WO 2016/138234 A1 | 9/2016 |
| WO | WO 2016/176307 A1 | 11/2016 |
| WO | WO 2016/210173 A1 | 12/2016 |
| WO | WO 2017/066096 A1 | 4/2017 |
| WO | WO 2017/184367 A1 | 10/2017 |

OTHER PUBLICATIONS

U.S. Appl. No. 15/138,802, Apr. 26, 2016, McMillen.
U.S. Office Action dated Sep. 12, 2012 issued in U.S. Appl. No. 12/904,657.
U.S. Office Action dated Apr. 15, 2013 issued in U.S. Appl. No. 12/904,657.
U.S. Notice of Allowance dated Nov. 8, 2013 issued in U.S. Appl. No. 12/904,657.
U.S. Office Action dated Mar. 12, 2015 issued in U.S. Appl. No. 14/173,617.
U.S. Notice of Allowance dated May 1, 2015 issued in U.S. Appl. No. 14/173,617.
U.S. Office Action dated Mar. 10, 2016 issued in U.S. Appl. No. 14/727,619.
U.S. Final Office Action dated Jul. 18, 2016 issued in U.S. Appl. No. 14/727,619.
U.S. Office Action dated Apr. 2, 2015 issued in U.S. Appl. No. 13/799,304.
U.S. Notice of Allowance dated Apr. 24, 2015 issued in U.S. Appl. No. 13/799,304.
U.S. Office Action dated Sep. 1, 2015 issued in U.S. Appl. No. 14/728,872.
U.S. Final Office Action dated Mar. 9, 2016 issued in U.S. Appl. No. 14/728,872.
U.S. Office Action dated Jun. 22, 2016 issued in U.S. Appl. No. 14/728,872.
U.S. Office Action dated Jul. 25, 2016 issued in U.S. Appl. No. 14/728,873.
U.S. Office Action dated Mar. 9, 2016 issued in U.S. Appl. No. 14/299,976.
U.S. Final Office Action dated Jul. 6, 2016 issued in U.S. Appl. No. 14/299,976.
U.S. Office Action dated Jan. 13, 2016 issued in U.S. Appl. No. 14/464,551.
U.S. Notice of Allowance dated Jun. 23, 2016 issued in U.S. Appl. No. 14/464,551.
U.S. Office Action dated Jun. 28, 2016 issued in U.S. Appl. No. 14/671,844.
U.S. Office Action dated May 20, 2016 issued in U.S. Appl. No. 14/928,058.
PCT International Search Report dated May 27, 2011, issued in PCT/US2010/052701.
PCT International Preliminary Report on Patentability and Written Opinion dated Apr. 26, 2012, issued in PCT/US2010/052701.

(56) References Cited

OTHER PUBLICATIONS

Japanese Office Action dated Feb. 25, 2014 issued in JP 2012-534361.
PCT International Search Report and Written Opinion dated Sep. 3, 2015 issued in PCT/US2015/029732.
PCT International Search Report and Written Opinion dated May 26, 2016 issued in PCT/US2016/019513.
PCT International Search Report and Written Opinion dated Apr. 14, 2016 issued in PCT/US2015/058370.
"Electronic Foot Size Measuring Devices," *Sensatech Research LTD., Custom Electronic Sensing Solutions*, Registered Office: 4 Heath Square, Boltro Road, Haywards Heath, RH16 1BL Company Registration No. 4524018 Cardiff [retrieved at http:www.electronicsarena.co.uk/companies/sensatech-research/products/electronic-foot-size-measureing-devices on Sep. 17, 2015], 3 pages.
"iStep® Digital Foot Scan," (© 2002-2015) [retrieved at http://www.foot.com/site/iStep on Sep. 17, 2015], 1 page.
"Podotech Elftman," and Podotech Elftman Brochure (UK Version) [retrieved at http://www.podotech.com/diagnostics/podotech-elftman-2/ on Sep. 17, 2015] podo+tech®, Foot Care Technology Solutions, 7 pages.
Roh, Jung-Sim et al. (2011) "Robust and reliable fabric and piezoresistive multitouch sensing surfaces for musical controllers," from Alexander Refsum Jensenius, Recorded at: *11th International Conference on New Interfaces for Musical Expression* May 30-Jun. 1, 2011, Oslo, Norway, a vimeo download at http://vimeo.com/26906580.
"The Emed®-Systems," [retrieved at http://www.novel.de/novelcontent/emed on Sep. 17, 2015] novel.de, 4 pages.
U.S. Notice of Allowance dated Sep. 15, 2016 issued in U.S. Appl. No. 14/727,619.
U.S. Final Office Action dated Oct. 18, 2016 issued in U.S. Appl. No. 14/728,872.
U.S. Advisory Action dated Feb. 10, 2017 issued in U.S. Appl. No. 14/728,872.
U.S. Office Action dated May 19, 2017 issued in U.S. Appl. No. 14/728,872.
U.S. Office Action dated Dec. 30, 2016 issued in U.S. Appl. No. 14/728,873.
U.S. Final Office Action dated Mar. 31, 2017 issued in U.S. Appl. No. 14/728,873.
U.S. Advisory Action and Examiner initiated interview summary dated May 26, 2017 issued in U.S. Appl. No. 14/728,873.
U.S. Office Action dated Oct. 21, 2016 issued in U.S. Appl. No. 14/299,976.
U.S. Final Office Action dated Apr. 19, 2017 issued in U.S. Appl. No. 14/299,976.
U.S. Final Office Action dated Jun. 8, 2017 issued in U.S. Appl. No. 14/299,976.
U.S. Office Action dated Sep. 23, 2016 issued in U.S. Appl. No. 14/800,538.
U.S. Notice of Allowance dated Jan. 17, 2017 issued in U.S. Appl. No. 14/800,538.
U.S. Office Action dated Feb. 22, 2017 issued in U.S. Appl. No. 14/671,821.
U.S. Notice of Allowance dated Jul. 3, 2017 issued in U.S. Appl. No. 14/671,821.
U.S. Final Office Action dated Nov. 25, 2016 issued in U.S. Appl. No. 14/671,844.
U.S.Notice of Allowance dated Mar. 13, 2017 issued in U.S. Appl. No. 14/671,844.
U.S. Office Action dated Jan. 26, 2017 issued in U.S. Appl. No. 15/052,293.
U.S. Final Office Action dated May 2, 2017 issued in U.S. Appl. No. 15/052,293.
U.S. Notice of Allowance dated May 24, 2017 issued in U.S. Appl. No. 15/052,293.
U.S. Notice of Allowance [Supplemental Notice of Allowability] dated Jun. 20, 2017 issued in U.S. Appl. No. 15/052,293.
U.S. Final Office Action dated Jan. 6, 2017 issued in U.S. Appl. No. 14/928,058.
U.S. Notice of Allowance dated Mar. 16, 2017 issued in U.S. Appl. No. 14/928,058.
U.S. Office Action dated Jun. 23, 2017 issued in U.S. Appl. No. 15/190,089.
U.S. Office Action dated Dec. 27, 2016 issued in U.S. Appl. No. 15/287,520.
U.S. Notice of Allowance dated Mar. 27, 2017 issued in U.S. Appl. No. 15/287,520.
PCT International Preliminary Report on Patentability and Written Opinion dated Nov. 24, 2016 issued in PCT/US2015/029732.
PCT International Preliminary Report on Patentability and Written Opinion dated May 11, 2017 issued in PCT/US2015/058370.
PCT International Search Report and Written Opinion dated Sep. 15, 2016 issued in PCT/US2016/029528.
PCT International Search Report and Written Opinion dated Sep. 29, 2016 issued in PCT/US2016/039089.
PCT International Search Report and Written Opinion dated Jan. 19, 2017 issued in PCT/US2016/055997.
U.S. Appl. No. 15/479,103, filed Apr. 4, 2017, McMillen et al.
U.S. Appl. No. 15/621,935, filed Jun. 13, 2017, McMillen et al.
U.S. Appl. No. 15/630,840, filed Jun. 22, 2017, McMillen et al.
U.S. Notice of Allowance dated Oct. 16, 2017 issued in U.S. Appl. No. 14/728,872.
U.S. Office Action dated Aug. 25, 2017 issued in U.S. Appl. No. 14/728,873.
U.S. Final Office Action dated Dec. 22, 2017 issued in U.S. Appl. No. 14/728,873.
U.S. Office Action dated Sep. 1, 2017 issued in U.S. Appl. No. 14/299,976.
U.S. Notice of Allowance dated Sep. 22, 2017 issued in U.S. Appl. No. 15/052,293.
U.S. Notice of Allowance [Supplemental Notice of Allowability] dated Oct. 19, 2017 issued in U.S. Appl. No. 15/052,293.
U.S. Office Action dated Nov. 3, 2017 issued in U.S. Appl. No. 15/138,802.
U.S. Notice of Allowance dated Aug. 10, 2017 issued in U.S. Appl. No. 15/190,089.
PCT International Preliminary Report on Patentability and Written Opinion dated Sep. 8, 2017 issued in PCT/US2016/019513.
PCT International Preliminary Report on Patentability and Written Opinion dated Oct. 31, 2017 issued in PCT/US2016/029528.
PCT International Search Report and Written Opinion dated Aug. 14, 2017 issued in PCT/US2017/026812.
U.S. Appl. No. 15/835,131, filed Dec. 7, 2017, McMillen et al.
U.S. Office Action dated Mar. 26, 2018 issued in U.S. Appl. No. 14/728,873.
U.S. Notice of Allowance dated Feb. 22, 2018 issued in U.S. Appl. No. 14/299,976.
U.S. Final Office Action dated Mar. 1, 2018 issued in U.S. Appl. No. 15/138,802.
PCT International Preliminary Dec. 26, 2017 Report on Patentability and Written Opinion dated issued in PCT/US2016/039089.
U.S. Notice of Allowance dated Jul. 19, 2018 issued in U.S. Appl. No. 14/728,873.
U.S. Office Action dated Jul. 12, 2018 issued in U.S. Appl. No. 15/483,926.
U.S. Office Action dated Jul. 24, 2018 issued in U.S. Appl. No. 15/835,131.
U.S. Office Action dated Aug. 14, 2018 issued in U.S. Appl. No. 15/621, 935.
U.S. Advisory Action dated May 16, 2018 issued in U.S. Appl. No. 15/138,802.
U.S. Notice of Allowance dated Jul. 3, 2018 issued in U.S. Appl. No. 15/138,802.
PCT International Preliminary Report on Patentability and Written Opinion dated Apr. 26, 2018 issued in PCT/US2016/055997.
U.S. Appl. No. 15/986,649, filed May 22, 2018, McMillen et al.
U.S. Office Action dated Dec. 31, 2018 issued in U.S. Appl. No. 15/374,816.
U.S. Notice of Allowance dated Dec. 31, 2018 issued in U.S. Appl. 15/483,926.

(56) References Cited

OTHER PUBLICATIONS

U.S. Notice of Allowance dated Dec. 4, 2018 issued in U.S. Appl. 15/835,131.
U.S. Office Action dated Dec. 13, 2018 issued in U.S. Appl. 15/690,108.
Japanese Office Action dated Dec. 4, 2018 issued in JP 2016-566814.
PCT International Search Report and Written Opinion dated Nov. 8, 2018 issued in PCT/US2018/035848.

* cited by examiner

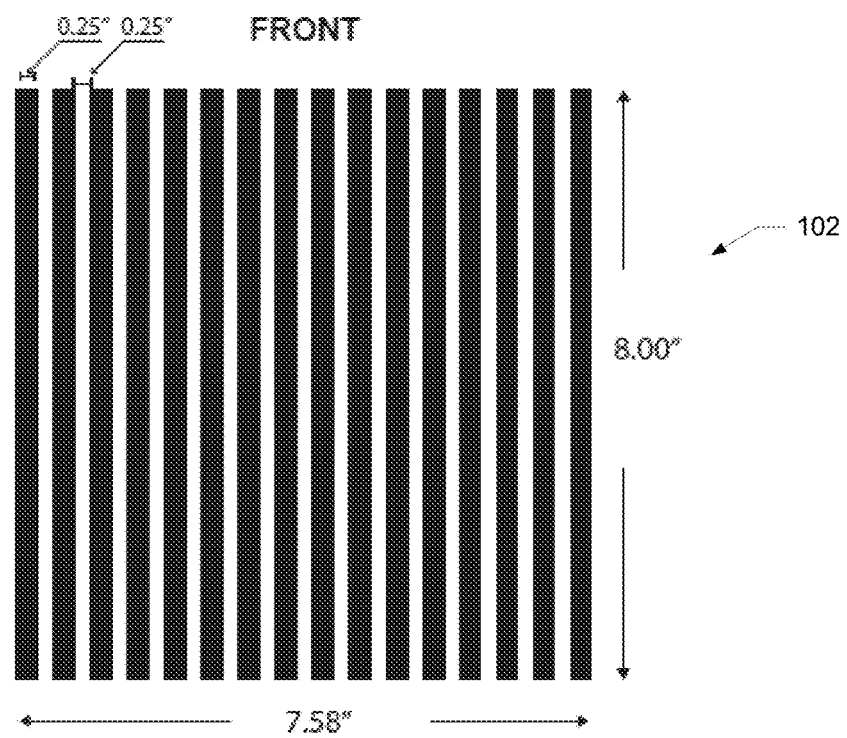
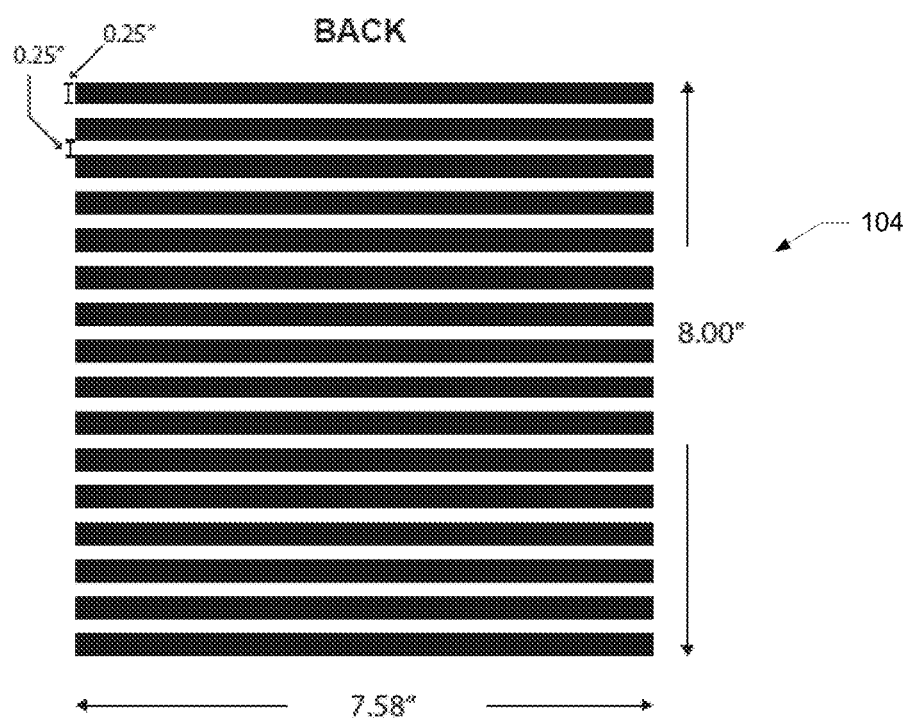
FIG. 1

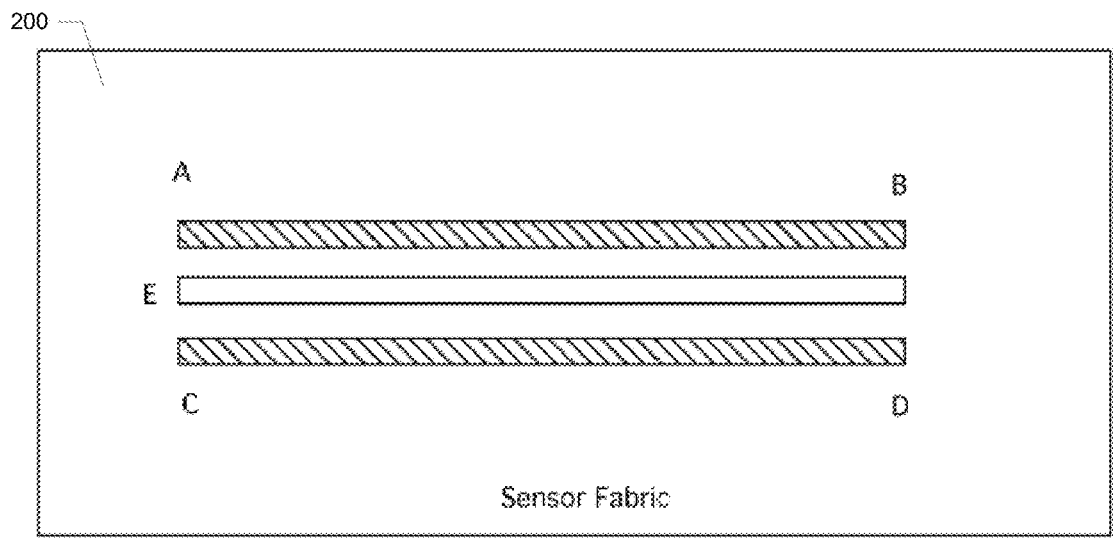

Unique electrical signal sent into points A, B, C, D succesively or sumultaneously. Conductors AB and CD are approx 10% of relaxed surface resistance of Sensor fabric.

Conductor E has near zero resistance andmeasures each of the signals based on increasing pressure to sensor material between elements which reduces resistance causing larger signals of A, B, C, D to be seen on E.

Using ratios of A - B and total Amplitude of A+B position and pressure can be determined.

Measuring ratios of above between signals A-B and C-D location of pressure can be determined between.

If wide contact point or multiple contact points appear along the conductors, a conductive plane behind sensor fabric will allow measurement of signals passed through the fabric to remove ambiguity.

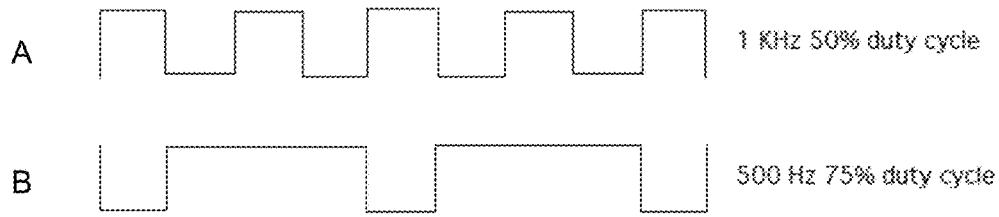

FIG. 2

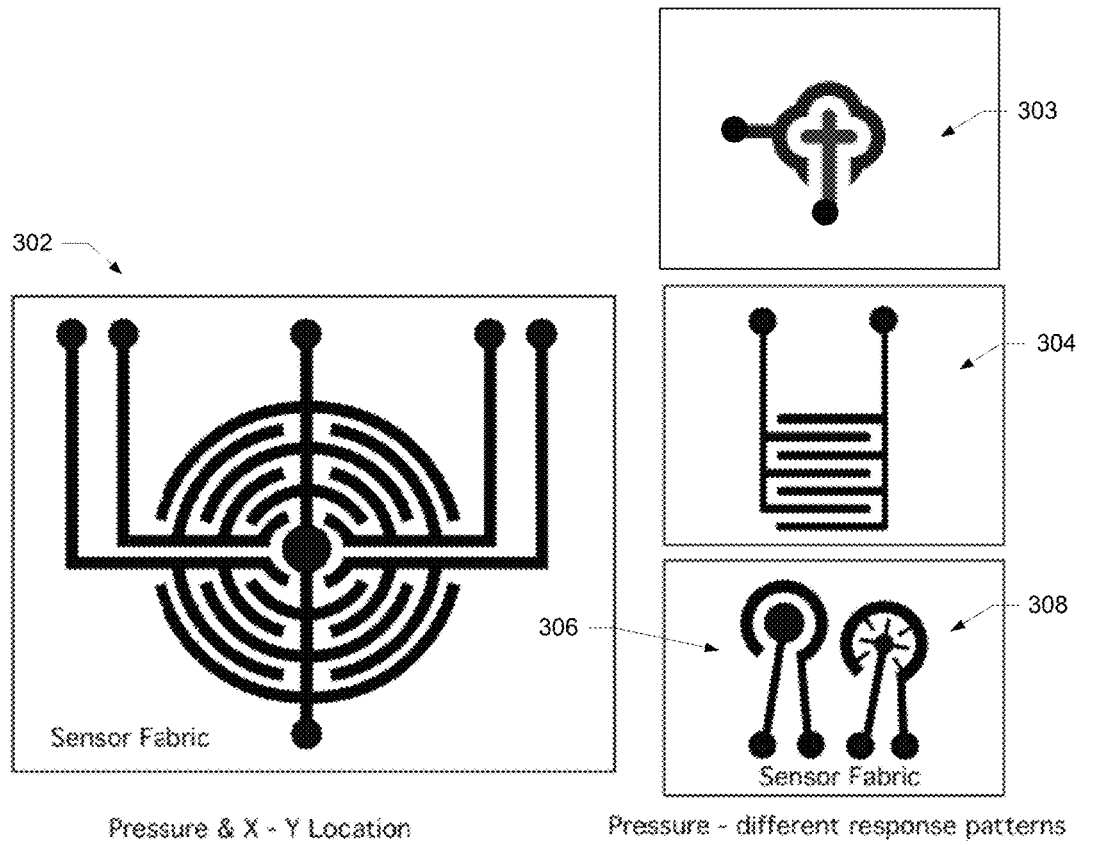
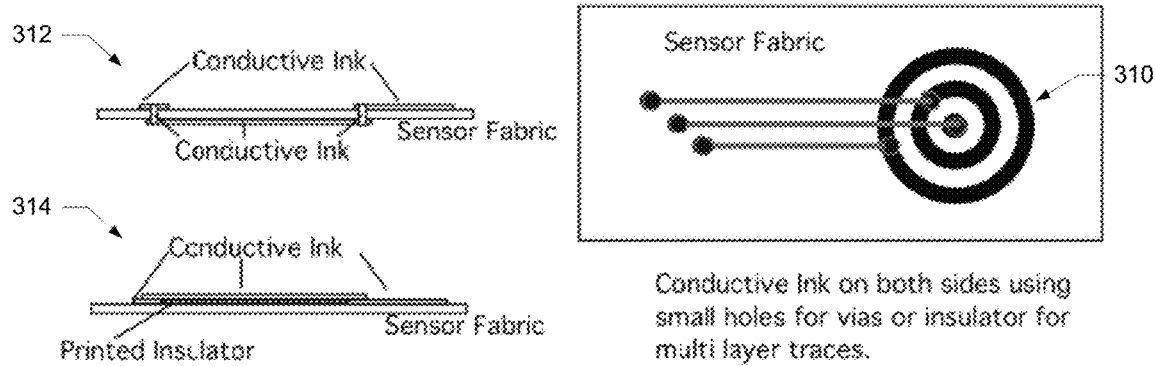
FIG. 3

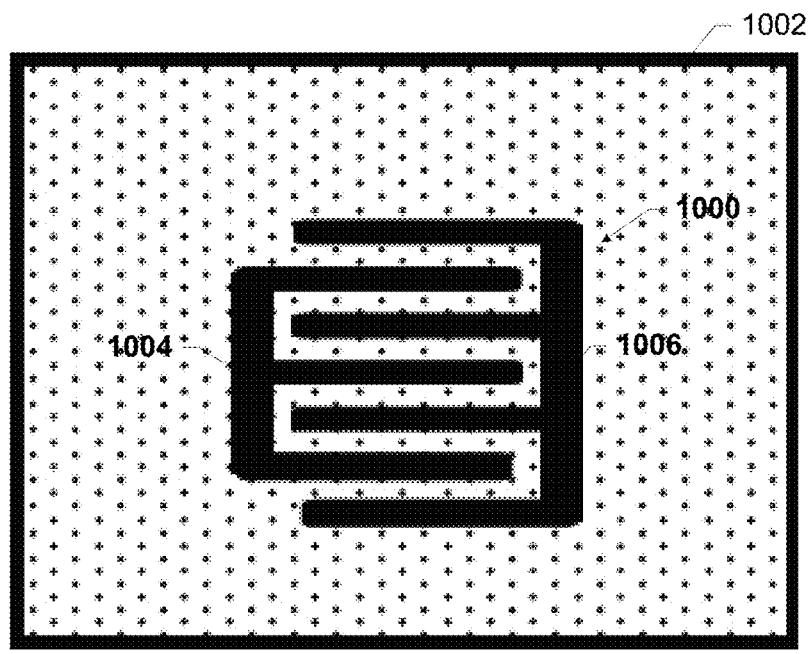
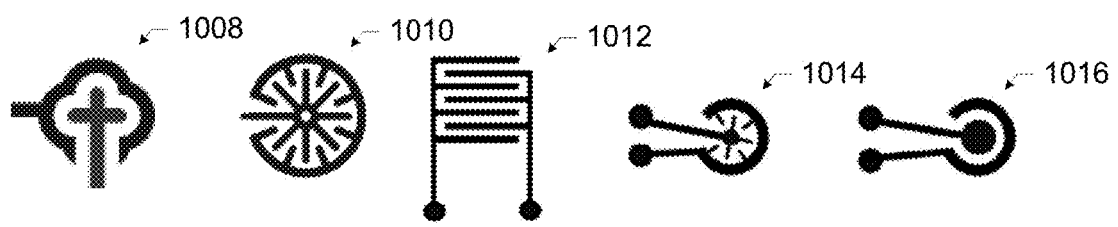
FIG. 10

FLEXIBLE SENSORS AND APPLICATIONS

RELATED APPLICATION DATA

The present application is a divisional application of and claims priority under 35 U.S.C. 120 to U.S. patent application Ser. No. 14/671,821 entitled Flexible Sensors and Applications filed on Mar. 27, 2015, which is a continuation-in-part of U.S. patent application Ser. No. 14/299,976 entitled Piezoresistive Sensors and Applications filed on Jun. 9, 2014. U.S. patent application Ser. No. 14/671,821 is also a non-provisional of and claims priority under 35 U.S.C. 119(e) to each of U.S. Provisional Patent Application No. 61/993,953 entitled Piezoresistive Sensors and Applications filed on May 15, 2014, U.S. Provisional Patent Application No. 62/057,130 entitled Interfaces for Conductors Integrated with Fabric or Other Flexible Substrates filed on Sep. 29, 2014, and U.S. Provisional Patent Application No. 62/072,798 entitled Flexible Sensors and Applications filed on Oct. 30, 2014. The entire disclosures of each of the foregoing applications is incorporated herein by reference for all purposes.

BACKGROUND

Demand is rapidly rising for technologies that bridge the gap between the computing devices and the physical world. These interfaces typically require some form of sensor technology that translates information from the physical domain to the digital domain. The "Internet of Things" contemplates the use of sensors in a virtually limitless range of applications, for many of which conventional sensor technology is not well suited.

SUMMARY

According to various implementations, sensors and applications of sensors are provided.

According to some implementations, an assembly includes a printed circuit board assembly (PCBA) including a plurality of pads. A flexible substrate includes a plurality of conductors. The plurality of conductors are aligned with the plurality of pads. Conductive adhesive provides electrical connections between the pads of the PCBA and the conductors of the substrate. A plurality of mechanical members extend through apertures in the PCBA and the substrate. The mechanical members are deformed to secure the PCBA to the substrate.

According to some implementations, a method is provided for connecting a printed circuit board assembly (PCBA) including a plurality of pads to a flexible substrate including a plurality of conductors. A conductive adhesive is deposited on one or both of the pads of the PCBA and the conductors of the flexible substrate. The pads of the PCBA are aligned with the conductors of the flexible substrate, thereby making electrical connections between the pads of the PCBA and the conductors of the flexible substrate via the conductive adhesive. Mechanical members are inserted through apertures in the PCBA and the flexible substrate. The mechanical members are deformed to secure the PCBA to the flexible substrate.

According to some implementations, an assembly includes a printed circuit board assembly (PCBA) including a plurality of pads. A flexible substrate includes a plurality of conductors. The plurality of conductors are aligned with the plurality of pads. A plurality of mechanical members extend through apertures in the PCBA and the substrate. The mechanical members are deformed to secure the PCBA to the substrate. Electrical connections between the pads of the PCBA and the conductors of the substrate are maintained by mechanical force resulting from securing of the PCBA to the substrate.

According to some implementations, a sensor includes a flexible piezoresistive substrate and a sensor trace pattern including two or more conductive traces formed directly on the piezoresistive substrate. Resistance between the conductive traces varies with distortion or deformation of the piezoresistive substrate.

A further understanding of the nature and advantages of various implementations may be realized by reference to the remaining portions of the specification and the drawings.

BRIEF DESCRIPTION OF THE DRAWINGS

FIG. 1 illustrates a two-sided sensor array.

FIG. 2 illustrates another sensor configuration and a technique for acquiring sensor data.

FIG. 3 illustrates various sensor configurations.

FIG. 10 shows examples of trace patterns that may be integrated with a flexible substrate.

DETAILED DESCRIPTION

Figure 4:
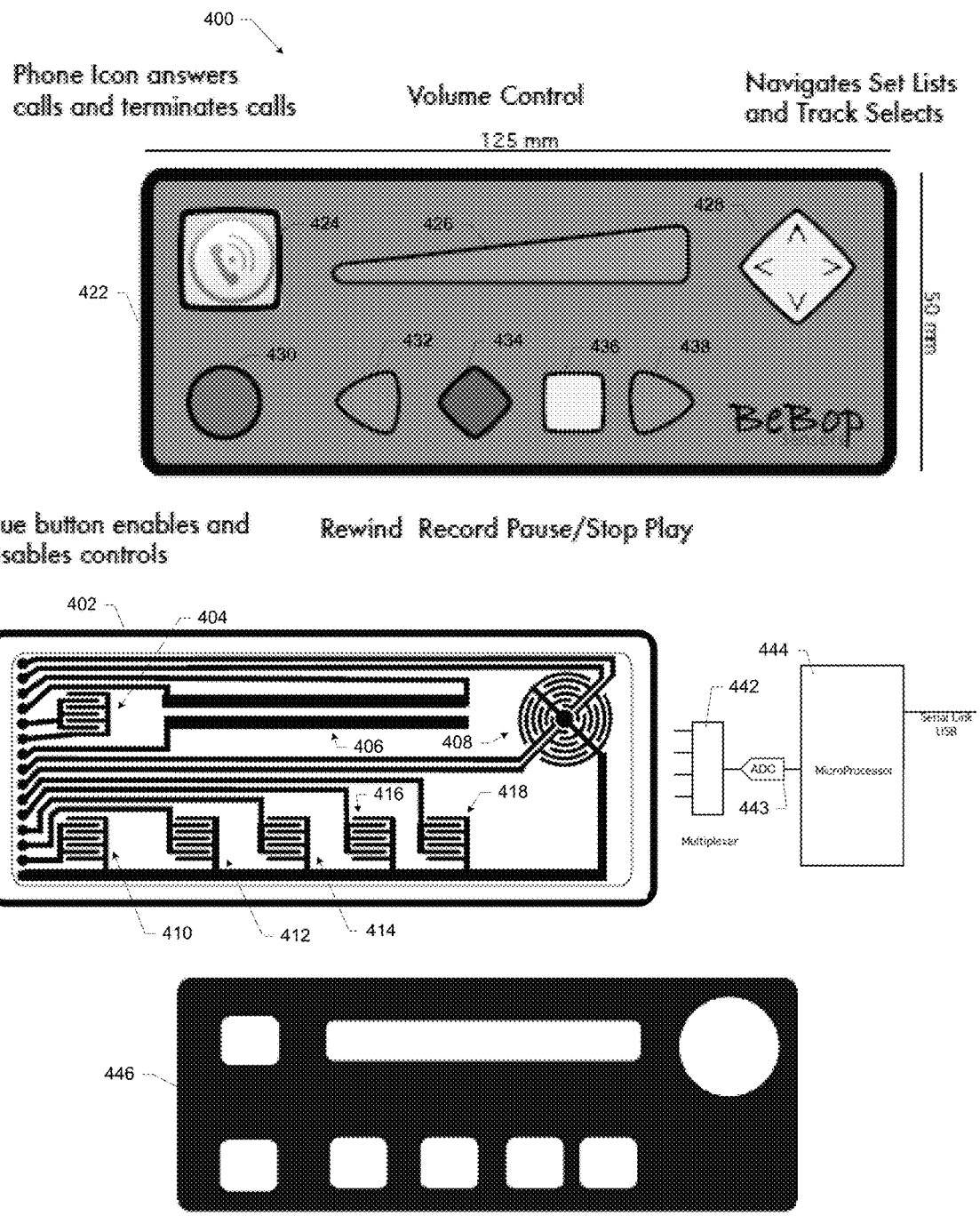
FIG. 4 illustrates a controller that employs a variety of sensor configurations.

Sensors incorporating piezoresistive materials are described in this disclosure. Specific implementations are described below including the best modes contemplated. Examples of these implementations are illustrated in the accompanying drawings. However, the scope of this disclosure is not limited to the described implementations. Rather, this disclosure is intended to cover alternatives, modifications, and equivalents of these implementations. In the following description, specific details are set forth in order to provide a thorough understanding of the described implementations. Some implementations may be practiced without some or all of these specific details. In addition, well known features may not have been described in detail to promote clarity.

Piezoresistive materials include any of a class of materials that exhibit a change in electrical resistance in response to mechanical force or pressure applied to the material. One class of sensors described herein includes conductive traces formed directly on or otherwise integrated with a flexible substrate of piezoresistive material, e.g., a piezoresistive fabric or other flexible material. When force or pressure is applied to such a sensor, the resistance between traces connected by the piezoresistive material changes in a time-varying manner that is representative of the applied force. A signal representative of the magnitude of the applied force is generated based on the change in resistance. This signal is captured via the conductive traces (e.g., as a voltage or a current), digitized (e.g., via an analog-to-digital converter), processed (e.g., by an associated processor or controller or suitable control circuitry), and mapped (e.g., by the associated processor, controller, or control circuitry) to a control function that may be used in conjunction with virtually any type of process, device, or system. In some implementations, arrays of conductive traces having various configurations are used to determine the direction and/or velocity of the applied force in one or more dimensions (e.g., in addition to the magnitude of the force or pressure).

Printing, screening, depositing, or otherwise forming conductive traces directly onto flexible piezoresistive material allows for the creation of a sensor or sensor array that fits any arbitrary shape or volume. The piezoresistive material may be any of a variety of woven and non-woven fabrics having piezoresistive properties. Implementations are also contemplated in which the piezoresistive material may be any of a variety of flexible, stretchable, or otherwise deformable materials (e.g., rubber, or a stretchable fabric such as spandex or open mesh fabrics) having piezoresistive properties. The conductive traces may be formed using any of a variety of conductive inks or paints. Implementations are also contemplated in which the conductive traces are formed using any flexible conductive material that may be formed on the flexible piezoresistive material. It should therefore be understood that, while specific implementations are described with reference to specific materials and techniques, the scope of this disclosure is not so limited.

Both one-sided and two-side implementations are contemplated, e.g., conductive traces can be printed on one or both sides of the piezoresistive fabric. As will be understood, two-sided implementations may require some mechanism for connecting conductive traces on one side of the fabric to those on the other side. Some implementations use vias in which conductive ink or paint is flowed through the vias to establish the connections. Alternatively, metal vias or rivets may make connections through the fabric.

Both single and double-sided implementations may use insulating materials formed over conductive traces. This allows for the stacking or layering of conductive traces and signal lines, e.g., to allow the routing of signal line to isolated structures in a manner analogous to the different layers of a printed circuit board.

Routing of signals on and off the piezoresistive fabric may be achieved in a variety of ways. A particular class of implementations uses elastomeric connectors (e.g., ZEBRA® connectors) which alternate conductive and non-conductive rubber at a density typically an order of magnitude greater than the width of the conductive traces to which they connect (e.g., at the edge of the fabric). Alternatively, a circuit board (possibly made of a flexible material such as Kapton), or a bundle of conductors may be riveted to the fabric. The use of rivets may also provide mechanical reinforcement to the connection.

Matching conductive traces or pads on both the piezoresistive material and a circuit board can be made to face each. A layer of conductive adhesive (e.g., a conductive epoxy such as Masterbond EP79 from Masterbond, Inc. of Hackensack, N.J.) can be applied to one of the surfaces and then mated to the other surface. The conductive traces or pads can also be held together with additional mechanical elements such as a plastic sonic weld or rivets. If conductive rivets are used to make the electrical connections to the conductive traces of the piezoresistive fabric, the conductive adhesive may not be required. Conductive threads may also be used to connect the conductive traces of the fabric to an external assembly.

According to a particular class of implementations, the piezoresistive material is a pressure sensitive fabric manufactured by Eeonyx, Inc., of Pinole, Calif. The fabric includes conductive particles that are polymerized to keep them suspended in the fabric. The base material is a polyester felt selected for uniformity in density and thickness as this promotes greater uniformity in conductivity of the finished piezoresistive fabric. That is, the mechanical uniformity of the base material results in a more even distribution of conductive particles when the slurry containing the conductive particles is introduced. The fabric may be woven. Alternatively, the fabric may be non-woven such as, for example, a calendared fabric e.g., fibers, bonded together by chemical, mechanical, heat or solvent treatment. Calendared material presents a smoother outer surface which promotes more accurate screening of conductive inks than a non-calendared material.

The conductive particles in the fabric may be any of a wide variety of materials including, for example, silver, copper, gold, aluminum, carbon, etc. Some implementations may employ carbon graphenes that are formed to grip the fabric. Such materials may be fabricated using techniques described in U.S. Pat. No. 7,468,332 for Electroconductive Woven and Non-Woven Fabric issued on Dec. 23, 2008, the entire disclosure of which is incorporated herein by reference for all purposes. However, it should again be noted that any flexible material that exhibits a change in resistance or conductivity when pressure is applied to the material and on which conductive traces may be printed, screened, deposited, or otherwise formed will be suitable for implementation of sensors as described herein.

Conductive particles may be introduced to the fabric using a solution or slurry, the moisture from which is then removed. According to some implementations, the way in which the moisture is removed from the fabric may also promote uniformity. For example, using an evenly distributed array of vacuum heads or ports to pull the moisture from the fabric reduces the concentrations of conductive particles around individual vacuum heads or ports. The vacuum heads or ports may be arranged in 1 or 2 dimensional arrays; the latter being analogized to a reverse air hockey table, i.e., an array of vacuum ports which pull air in rather than push air out.

Implementations are also contemplated in which the uniformity of the piezoresistive fabric is not necessarily very good. Such implementations may use multiple, closely-spaced sensors operating in parallel, the outputs of which can be averaged to get more accurate and/or consistent readings.

According to a particular class of implementations, conductive traces having varying levels of conductivity are formed on the piezoresistive material using conductive silicone-based inks manufactured by, for example, E.I. du Pont de Nemours and Company (DuPont) of Wilmington, Del., and/or Creative Materials of Ayer, Mass. An example of a conductive ink suitable for implementing highly conductive traces for use with various implementations is product number 125-19 from Creative Materials, a flexible, high temperature, electrically conductive ink. Examples of conductive inks for implementing lower conductivity traces for use with various implementations are product numbers 7102 and 7105 from DuPont, both carbon conductive compositions. Examples of dielectric materials suitable for implementing insulators for use with various implementations are product numbers 5018 and 5036 from DuPont, a UV curable dielectric and an encapsulant, respectively. These inks are flexible and durable and can handle creasing, washing, etc. The degree of conductivity for different traces and applications is controlled by the amount or concentration of conductive particles (e.g., silver, copper, aluminum, carbon, etc.) suspended in the silicone. These inks can be screen printed or printed from an inkjet printer. Another class of implementations uses conductive paints (e.g., carbon particles mixed with paint) such as those that are commonly used for EMI shielding and ESD protection.

One example of a two-sided implementation of a sensor array is shown in FIG. 1 and has an array 102 of parallel conductive traces oriented in one direction printed on one side of the piezoresistive fabric, and another array 104 oriented at 90 degrees to the first array printed on the other side of the fabric. This implementation takes advantage of the fact that the piezoresistive fabric is conductive through its thickness (in addition to laterally and across its surface) to implement a pressure sensitive X-Y matrix. By sequentially driving the array on one side of the piezoresistive material and sequentially scanning the array on the other side, both the position and force of a touch event on the array can be detected. Again, because of the sequential selection and activation of the traces, such a configuration is capable of detecting multiple touch events substantially simultaneously. As will be understood, the applications for such a sensor array are virtually limitless.

As will be understood by those of skill in the art, a variety of techniques may be employed to acquire data from sensors constructed as described herein. Some of these techniques may involve a simple measurement of a change in resistance (as determined from a voltage or current) between two conductive traces having the same or similar conductivity. However, for sensors having arrays that include many conductive traces, this may require an unacceptable number of signal lines to route signals both to and from the sensor array. Therefore, according to a particular class of implementations, conductive traces formed on piezoresistive material and having different levels of conductivity are driven and interrogated with signal patterns that reduce the number of signal lines required to achieve sensor configurations that are sensitive to location, pressure, direction, and velocity of applied force.

FIG. 2 illustrates an example of such an implementation intended to function as a slider control but with many fewer signal lines than might otherwise be necessary to achieve this functionality. Adjacent (in this case substantially parallel) conductive traces are formed on piezoresistive fabric 200 with one (E) being highly conductive, e.g., near-zero resistance, and the other (AB) being less conductive, e.g., about 100 ohms from A to B if the resistance between traces AB and E without pressure is about 1K ohms (e.g., approximately 10% of the relaxed surface resistance of the piezoresistive fabric). The less conductive trace is driven at opposing ends by different signals A and B (e.g., by one or more signal generators). Pressure on the piezoresistive material reduces the resistance between the two traces which, depending on the location, results in different contributions from signals A and B measured in a mixed signal on the highly conductive trace E. The overall amplitude of the mixed signal also increases with pressure.

According to a particular class of implementations, signals A and B are different pulse trains of the same amplitude; e.g., one at 1 kHz, one with a 50% duty cycle, and the other at 500 Hz with a 75% duty cycle as shown in FIG. 2. The phases of the two pulse trains are synchronized to avoid zero volts being applied to the less conductive trace. Location information can be derived from the mixed signal measured on E as follows. The signal on E is sampled by an A/D converter (e.g., oversampled by a factor of two or more relative to the frequency of the inputs). An inexpensive, general-purpose processor may be employed that can read up to 40 signals with up to 10-bits of resolution, and take 500K samples per second. The same general processor may drive the conductive traces. Thus, arrays with large numbers of sensors may be constructed relatively inexpensively.

The processor evaluates specific amplitudes at specific times that are correlated with the values of signals A and B at those times. The relative contribution from each signal is determined by selecting closely-spaced samples of the mixed signal at times when the respective signals are each known to have a particular value or characteristic, e.g., full amplitude. The ratio of those two measurements represents the relative contributions of each signal to the mixed signal that, in turn, can be mapped to a location between the end points of the AB trace. The pressure or force of the touch event can be determined by measuring peak values of the sampled mixed signal (e.g., the total amplitude of contributions from A and B). With this configuration, a pressure sensitive slider can be implemented with only 3 signal lines required to drive the traces and acquire the signal.

According to a particular implementation and as shown in FIG. 2, a second conductive trace CD runs parallel to trace E on the opposing side from trace AB. As with trace AB, the opposing ends of this additional conductive trace are driven with signals C and D; each different from the other as well as signals A and B. As a result, the mixed signal on trace E includes contributions from each of the four signals. This mixed signal may be processed for one or both of the signal pairs in a manner similar to that described above to determine the location of a touch event along the longitudinal axis of the array. The relative amplitudes of the two signal pairs (e.g., derived by measuring amplitudes for the combination of signals A and B and the combination of signals C and D) represent the location of the touch event along the latitudinal axis of the array. This enables measuring of the location of the touch event in two dimensions. This might enable, for example, the capture of a sideways rocking motion of a finger on a key. As with the example described above, the pressure of the touch event may be determined by measuring peak values of the sampled mixed signal. If a wide contact point or multiple contact points appear along the conductors, a conductive plane behind the piezoresistive fabric may allow measurement of signals passed through the fabric to remove ambiguity. In this way, an XYZ sensor may implemented with five traces (with the Z axis representing the force of the touch event).

FIG. 3 shows a variety of trace patterns formed on flexible piezoresistive material, e.g., conductive ink on piezoresistive fabric, for different applications. Trace pattern 302 implements a four-quadrant sensor that operates similarly to those described, for example, in U.S. patent application Ser. No. 12/904,657 entitled Foot-Operated Controller, now U.S. Pat. No. 8,680,390, and U.S. patent application Ser. No. 13/799,304 entitled Multi-Touch Pad Controller, published as U.S. Patent Publication No. 2013/0239787, the entire disclosures of which are incorporated herein by reference for all purposes. In addition to detecting the occurrence and force of touch events, such a sensor may also be configured to determine the direction and velocity of motion over the quadrants including, for example, both linear and rotational motion relative to the surface of the sensor. Trace patterns 303 (clover and cruciform configuration), 304, 306 and 308 implement sensors that measure the occurrence and force of touch events with different response curves and dynamic ranges resulting from the different configurations.

Trace pattern 310 is used to illustrate both single and double-sided implementations that use either vias or rivets through the piezoresistive material (e.g., configuration 312), insulating materials formed over conductive traces (e.g., configuration 314), or both. As discussed above, such mechanisms enable complex patterns of traces and routing of signals in a manner analogous to the different layers of a printed circuit board.

It will be appreciated that sensors and sensor arrays designed as described in this disclosure may be employed in a very broad and diverse range of applications in addition to those described. One class of applications includes a wide variety of wearable electronics in which sensing and/or instrumentation components and control and/or processing components are integrated with articles of clothing. One example of such an application is a controller 400 for a smart phone or a digital media player as shown in FIG. 4. Controller 400 may be implemented with an underlying piezoresistive substrate 402 with conductive traces patterns 404-418 formed directly on the substrate to implement sensors that provide different types of controls. The trace patterns are aligned with a particular icon representing the control on an overlying substrate 422 with which a user interacts (i.e., icons 424-438). Alternatively, trace patterns 404-418 may be formed on the opposite side of the same substrate from icons 424-438. The substrate(s) from which controller 400 is constructed may be a piezoresistive fabric that may be incorporated, for example, in articles of clothing, e.g., in the sleeve of a shirt or jacket.

As described elsewhere herein, when pressure is applied to one of the controls, a resulting signal (captured via the corresponding traces) may be digitized and mapped by associated processing circuitry (e.g., multiplexer 442, A-D converter 443, and processor 444) to a control function associated with a connected device, e.g., the smart phone or media player (not shown) via, for example, a USB or Bluetooth connection. As will be appreciated, similar conversion and processing circuitry may be employed with any of the sensor configurations described herein.

In the depicted implementation, trace pattern 404 corresponds to icon 424 and implements a button control that allows the user to answer or terminate calls on his smart phone. Trace pattern 406 corresponds to icon 426 and implements a slider (e.g., such as the one described above with reference to FIG. 2) for volume control of, for example, a media player. Trace pattern 408 corresponds to icon 428 and implements a four-quadrant sensor that may be used for navigation of, for example, set lists, track queues, etc. Trace pattern 410 corresponds to icon 430 and implements an enable/disable control by which controller 400 may be enabled and disabled. Trace patterns 412-418 correspond to icons 432-438, respectively, and implement various media player controls such as, for example, play, pause, stop, record, skip forward, skip back, forward and reverse high-speed playback, etc. As will be appreciated, this is merely one example of a wide variety of controllers and control functions that may be implemented in this manner.

According to a particular implementation, an insulating layer 446 may be printed or deposited on piezoresistive substrate 402 before any of trace patterns 404-418. As can be seen, openings in insulating layer 446 line up with the portions of the trace patterns intended to implement the corresponding control functions. These portions of the trace patterns are therefore printed or deposited directly on the underlying piezoresistive substrate. By contrast, the conductive traces that connect these portions of the trace patterns to the edge of the piezoresistive substrate for routing to the processing circuitry are printed or deposited on insulating layer 446. This will significantly reduce crosstalk noise between these conductors relative to an approach in which they are also printed on the piezoresistive substrate.

According to some implementations, interfaces and techniques are provided for making connections to electrical conductors that are integrated with fabric or other flexible substrates. Examples of fabrics and flexible substrates including conductors to which such connections may be made are described herein. However, it should be noted that the techniques and interfaces described herein are much more widely applicable and may be employed to make connections to conductors in any of a wide variety of applications. For example, while some implementations describe flexible substrates that include piezoresistive materials, other implementations are contemplated in which the flexible substrate to which connections are made is not and/or does not include a piezoresistive material.

Figure 5:
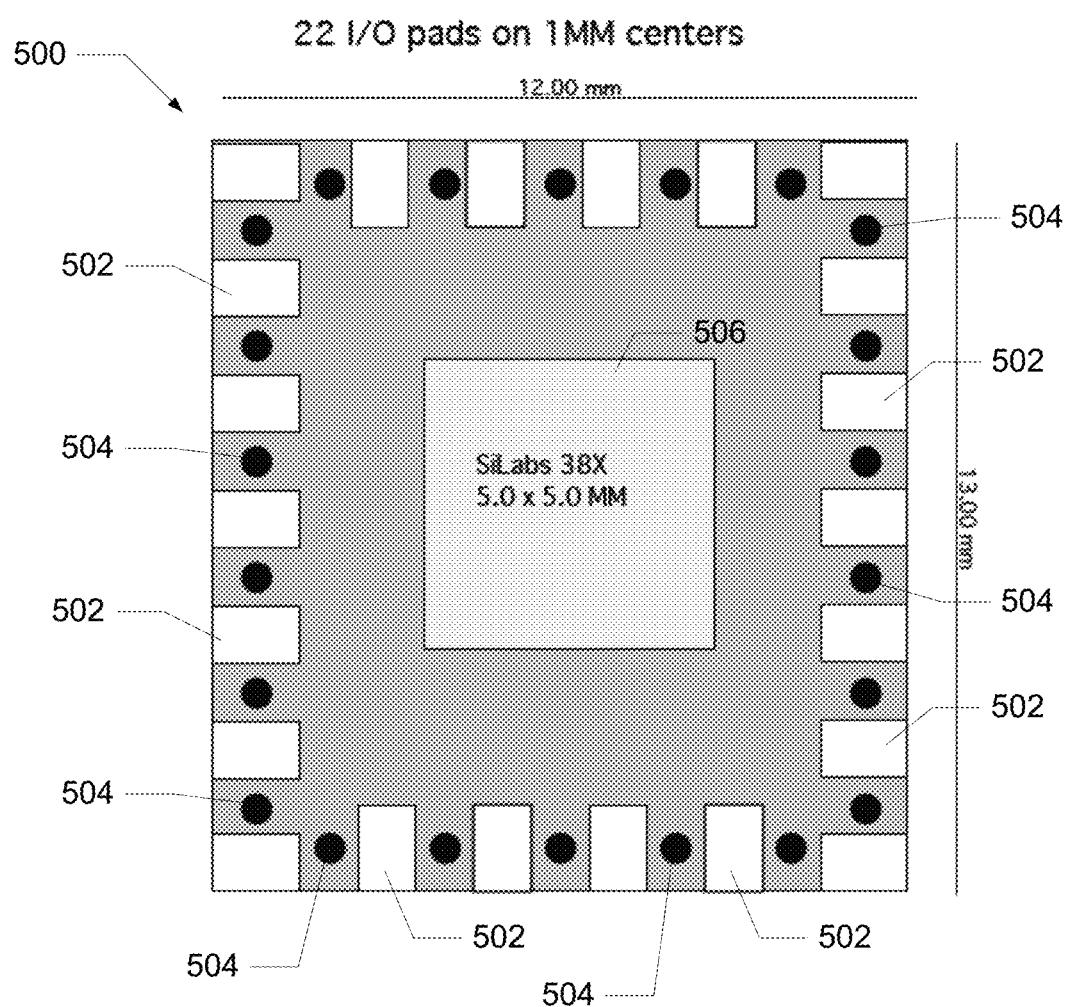
FIG. 5 shows an example of printed circuit board assembly (PCBA).

Specific implementations will now be described with reference to FIGS. 5-8. As will be understood, the specific details of these implementations are merely examples for the purpose of illustrating the techniques and interfaces enabled by this disclosure. FIG. 5 shows an example of printed circuit board assembly (PCBA) that may be connected to conductors that are part of a flexible substrate (not shown). In the depicted example, PCBA 500 is 12.0 mm×13.0 mm with a thickness of 0.2 mm. PCBA 500 has 22 I/O pads 502 with 1 mm spacing between the centers of adjacent pads, and 22 apertures 504, the purpose of which is described below. It should be noted that implementations are contemplated in which the spacing between the pads and the number and placement of the apertures may vary considerably. For example, the spacing of the pads may range below and above 1 mm to match the width and spacing of the conductors associated with the substrate to which the PCBA is connected. In another example, there may be more or fewer apertures for the mechanical features they accommodate. PCBA 500 is also shown as including a microcontroller 506 connected with I/O pads 502 via the internal conductors of PCBA 500 (not shown). As will be understood, the circuitry associated with PCBA 500 may include any kind of suitable circuitry and will vary considerably depending on the application.

Figure 6:
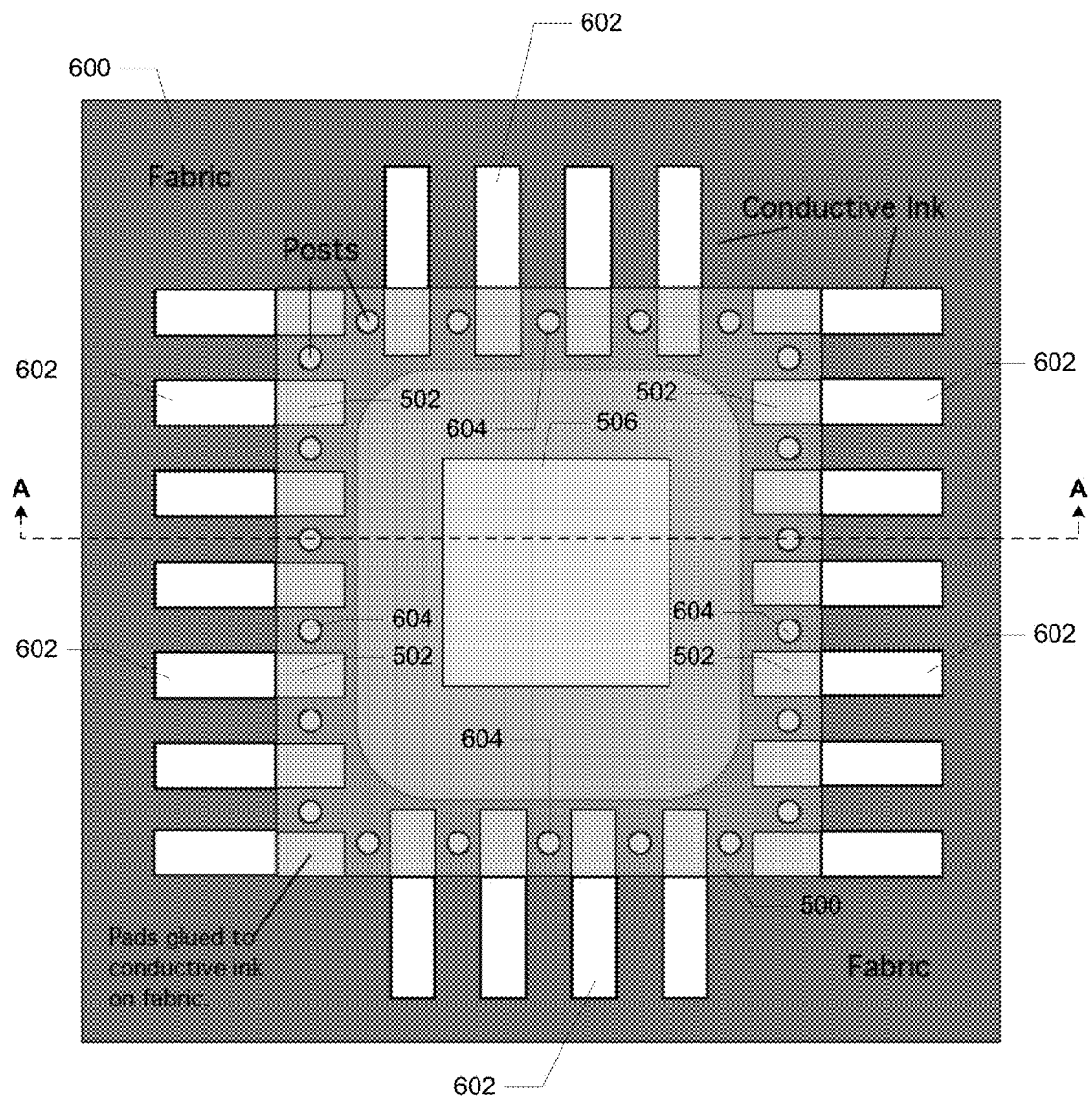
FIGS. 6-9 show PCBAs connected to conductors of a flexible substrate according to various implementations.

FIG. 6 shows PCBA 500 connected to fabric (or flexible substrate) 600 such that pads 502 of PCBA 500 are aligned with conductive traces 602 formed on fabric 600 and microcontroller 506 is aligned with an aperture in fabric 600. Conductive traces 602 may be, for example, conductive ink traces printed on fabric 600. Examples of conductive ink include product number 125-19 from Creative Materials (a flexible, high temperature, electrically conductive ink) and product numbers 7102 and 7105 from DuPont (both carbon conductive compositions). Traces 602 might also be formed using conductive paints (e.g., carbon particles mixed with paint) such as those that are commonly used for EMI shielding and ESD protection. Yet another alternative includes wires or conductive threads woven into or otherwise embedded in or attached to fabric 600. A wide variety of other conductors that are integrated with or on fabric 600 are within the scope of this disclosure.

According to a particular implementation, PCBA 500 is attached to fabric 600 as follows. A conductive adhesive (e.g., a conductive epoxy such as Masterbond EP79 from Masterbond, Inc. of Hackensack, N.J.) is screen printed over traces 602 on fabric 600. PCBA 500 is then positioned over fabric 600 such that pads 502 are aligned with traces 602 and microcontroller 506 is aligned with the aperture in fabric 600. In some cases PCBA 500 includes additional components (e.g., capacitors, resistors, diodes, or other active and passive devices and components). The aperture can be made to accommodate such components as well. The conductive adhesive secures each trace to its corresponding pad.

Figure 7:
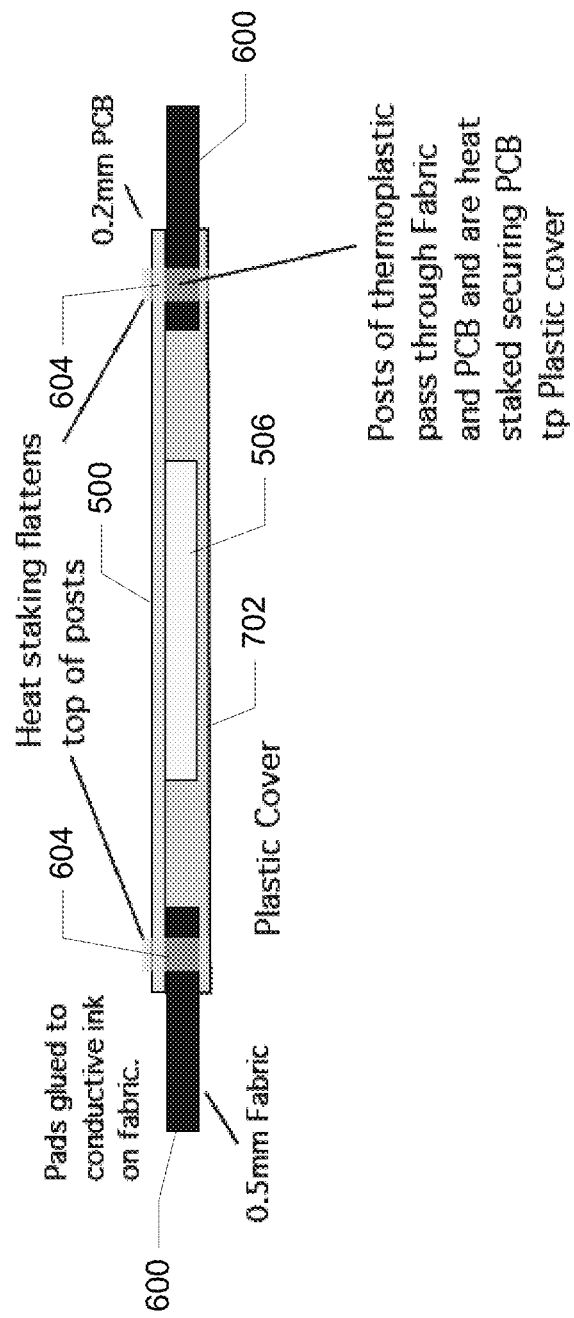

A plastic molded cover (not shown) is placed on the other side of fabric 600 from PCBA 500 with 0.6 mm posts 604 extending from the plastic cover and passing through both fabric 600 and PCBA 500. The tops of posts 604 are heat staked thereby flattening them out against the back side of PCBA 500 and securing the assembly. The conductive adhesive between traces 602 and pads 502 is allowed to dry. It should be noted that posts 604 may be a variety of structures capable of securing the assembly such as, for example, plastic or metal rivets, plastic sonic welds, etc. FIG. 7 shows a cross-section A-A of the assembly of FIG. 6 in which plastic cover 702 may be seen.

As will be appreciated, PCBA 500 may include any of a wide variety digital, analog, and mixed-signal circuitry as well as a variety of additional components including, for example, connectors to external circuits or systems (e.g., USB connectors), transceivers (e.g., Bluetooth), power components (e.g., batteries, power chip sets, solar cells, etc.), various electronic and mechanical components (e.g., capacitors, resistors, diodes, other active or passive devices or components, solder pads, posts, sockets, etc.). Other suitable components will be apparent to those of skill in the art for a given application.

In some implementations, multiple PCBAs may be integrated with fabric or a flexible substrate at multiple locations; including at an edge of the fabric or substrate, or surrounded by the fabric or substrate (as shown in FIG. 6). Where desired, the various components of multiple PCBAs may communicate with each other via any of a variety of protocols such as, for example, I²C (Inter-Integrated Circuit), SPI (SCSI Parallel interface), etc. The connections enabling this communication could be made via the conductors integrated with the fabric or flexible substrate (e.g., using conductive ink or paint) or using any of a variety of other available connection methods (both wired and wireless). According to some implementations, these and other conductors not actively involved with the functionality of the circuitry integrated with the fabric or flexible substrate may be isolated from that circuitry, e.g., by printing them on or integrating them with an insulating layer adjacent the fabric or flexible substrate.

Figure 8:
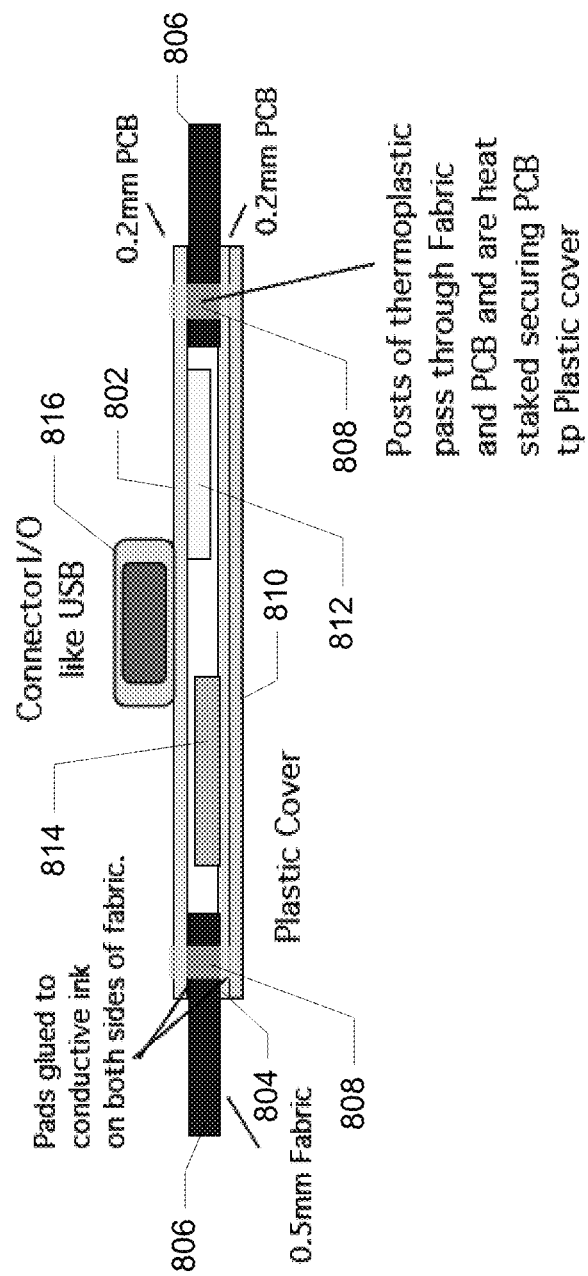

FIG. 8 shows a cross-section of another assembly in which the pads (not shown) of two PCBAs 802 and 804 are connected to conductive traces (not shown) on opposing sides of fabric (or flexible substrate) 806. As described above with reference to the assembly of FIGS. 6 and 7, the conductive traces on fabric 806 are aligned with and secured to the pads on PCBAs 802 and 804 using a conductive adhesive. Posts 808 extending from plastic cover 810 extend through apertures (not shown) in both of PCBAs 802 and 804 as well as fabric 806 to secure the assembly (e.g., through heat staking, sonic welding, rivet deformation, etc.). The assembly shown in FIG. 8 enables two-sided implementations in which the conductors of fabric 806 are accessible on both sides of the fabric and in which two PCBAs may be aligned on opposite sides of the fabric, each potentially having its own circuitry and/or components (e.g., components 812 and 814). PCBAs 802 and 804 can also be connected (e.g., using standard conductive rubber zebra strips or other suitable alternatives) to support board to board communication that need not pass through the fabric. The assembly of FIG. 8 also shows an example of a connector 816 to external systems or components (e.g., a USB connector) mounted on one side of PCBA 802.

It should be noted that implementations are contemplated in which a PCBA is secured to a flexible substrate without the use of a conductive adhesive to connect the pads of the PCBA to the traces of the flexible substrate. Instead, such implementations rely for these connections on the mechanical force resulting from the way in which the assembly components are secured together. For example, as an alternative to the implementation described above with reference to FIGS. 5-7, PCBA 500 may be aligned relative to fabric 600 such that pads 502 are aligned with traces 602 but without the use of the conductive adhesive. Instead, plastic cover 702 may be placed on the other side of fabric 600 from PCBA 500 with posts 604 extending from the plastic cover and passing through both fabric 600 and PCBA 500. The assembly is secured (including the electrical connections between PCBA pads and fabric traces) by the mechanical force resulting from securing the assemblies together (e.g., by the heat staking of posts 604). An alternative to the implementation of FIG. 8 may be similarly constructed without the use of conductive adhesive.

As described above, implementations enabled by the present disclosure may support a wide range of wearable electronics in which sensing and/or instrumentation components and control and/or processing components are integrated with articles of clothing, thereby enabling a virtually limitless range of applications. One example of such an application is controller 400 described above with reference to FIG. 4. According to a more specific implementation, the associated processing circuitry (e.g., multiplexer 442, A-D converter 443, and processor 444) is arranged on a PCBA (e.g., such as PCBA 500, 802, 804, etc.) and connected with trace patterns 404-418 and substrate(s) 402 and/or 422 using the techniques described herein.

Figure 9:
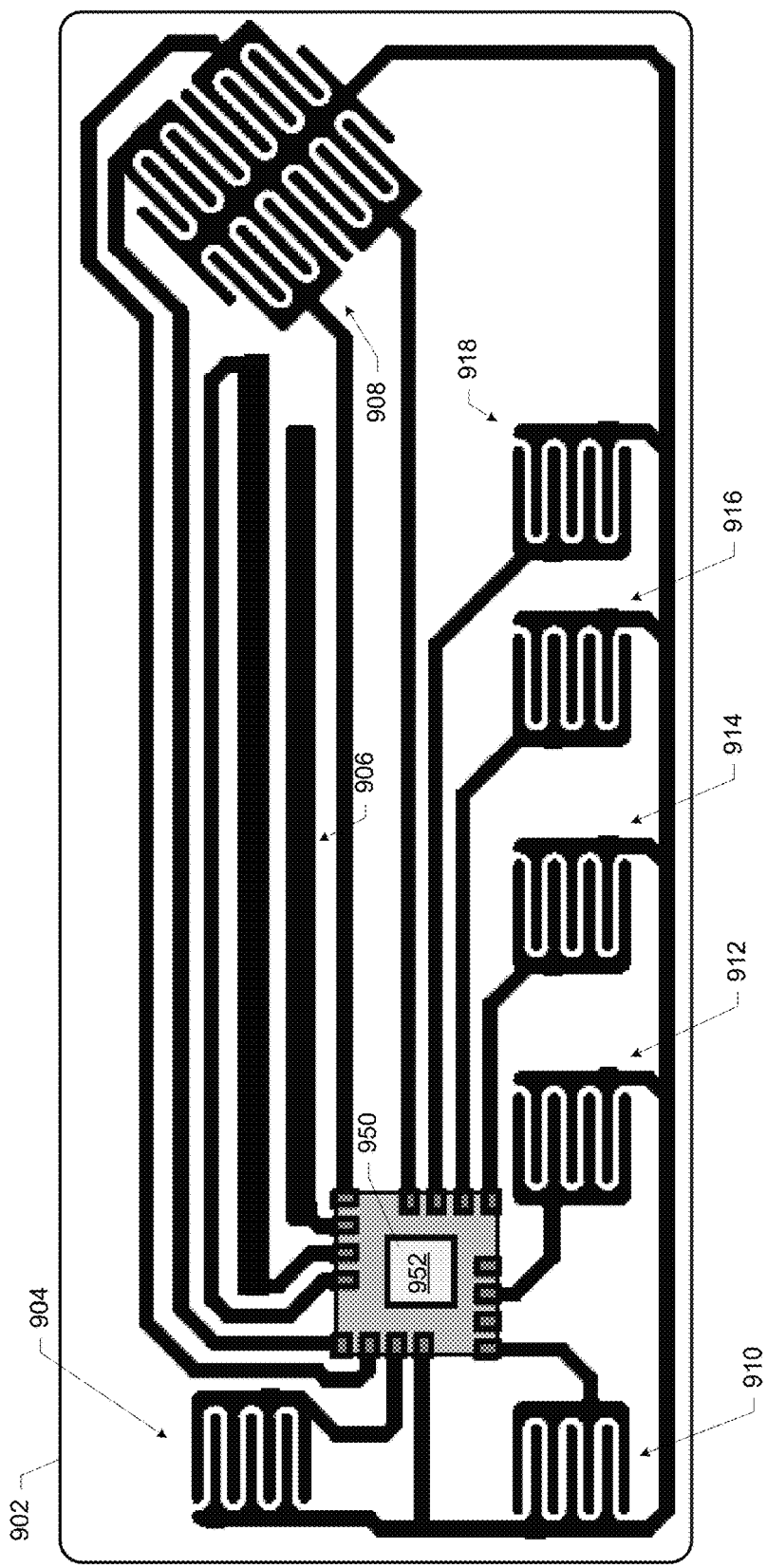

An alternative implementation of controller 400 may employ piezoresistive substrate 902 of FIG. 9 which includes conductive traces patterns 904-918 formed directly on the substrate to implement the sensors that provide the different types of controls described above. Substrate 902 may be a fabric or other type of flexible substrate. The trace patterns are aligned with the icons representing the controls on substrate 422 (i.e., icons 424-438). In this implementation, trace pattern 904 corresponds to icon 424, trace pattern 906 to icon 426, trace pattern 908 to icon 428, trace pattern 910 to icon 430, and trace patterns 912-918 to icons 432-438, respectively.

In contrast with the implementation of FIG. 4 in which the traces of substrate 402 are routed to the edge of the substrate, the processing circuitry associated with this controller is included on a PCBA that is surrounded by substrate 902 as shown. PCBA 950 is connected to substrate 902 such that pads of PCBA 950 are aligned with the conductive traces formed on substrate 902 and processing circuitry 952 is aligned with an aperture in substrate 902. The connections between the traces of substrate 902 and the pads of PCBA 950 may be made as described above with reference to FIGS. 5-8. And as described above with reference to FIG. 4, signals captured via the traces of substrate 902 may be digitized and mapped by processing circuitry 952 to a control function associated with one or more connected devices or systems (not shown). Other features of the implementation of FIG. 4 may also be used with implementations that employ substrate 902 and PCBA 950 including, for example, an insulating layer (e.g., like layer 446) to reduce crosstalk noise between conductors routing signals from the trace patterns to the PCBA.

As should be appreciated with reference to the present disclosure, forming sensors on flexible materials enables numerous useful devices. Many of these devices employ such sensors to detect the occurrence of touch events, the force or pressure of touch events, the duration of touch events, the location of touch events, the direction of touch events, and/or the speed of motion of touch events. This information is then used to effect a wide variety of controls and/or effects. Sensors formed on or integrated with flexible piezoresistive substrates may also be used to detect forces applied to or acting on the substrate that may or may not necessarily relate to or be characterized as touch events. The output signals from such sensors may be used to detect a variety of distortions and/or deformations of the substrate on which they are formed or with which they are integrated such as, for example, bends, stretches, torsions, rotations, etc. Examples of such distortions and/or deformations are described below with reference to accompanying figures. As will be understood, the specific details described are merely examples for the purpose of illustrating the techniques enabled by this disclosure.

FIG. 10 shows an example of a sensor trace pattern 1000 integrated with a flexible substrate 1002. Trace pattern 1000 includes a pair of conductive traces, one of which (e.g., trace 1004) provides a sensor signal to associated circuitry (not shown), and the other of which (e.g., trace 1006) is connected to ground or a suitable reference. Some representative examples of other trace patterns 1008-1016 that might be used in place of trace pattern 1000 are also shown. In some implementations, the traces of a trace pattern may be formed directly, e.g., by screening or printing, on the flexible substrate which might be, for example, a piezoresistive fabric. However, it should be noted that, among other things, the geometries of the sensor trace pattern(s), the number of traces associated with each sensor, the number, spacing, or arrangement of the sensors, the relationship of the sensors to the substrate, the number of layers or substrates, and the nature of the substrate(s) may vary considerably from application to application, and that the depicted configuration is merely one example for illustrative purposes.

Figure 11:
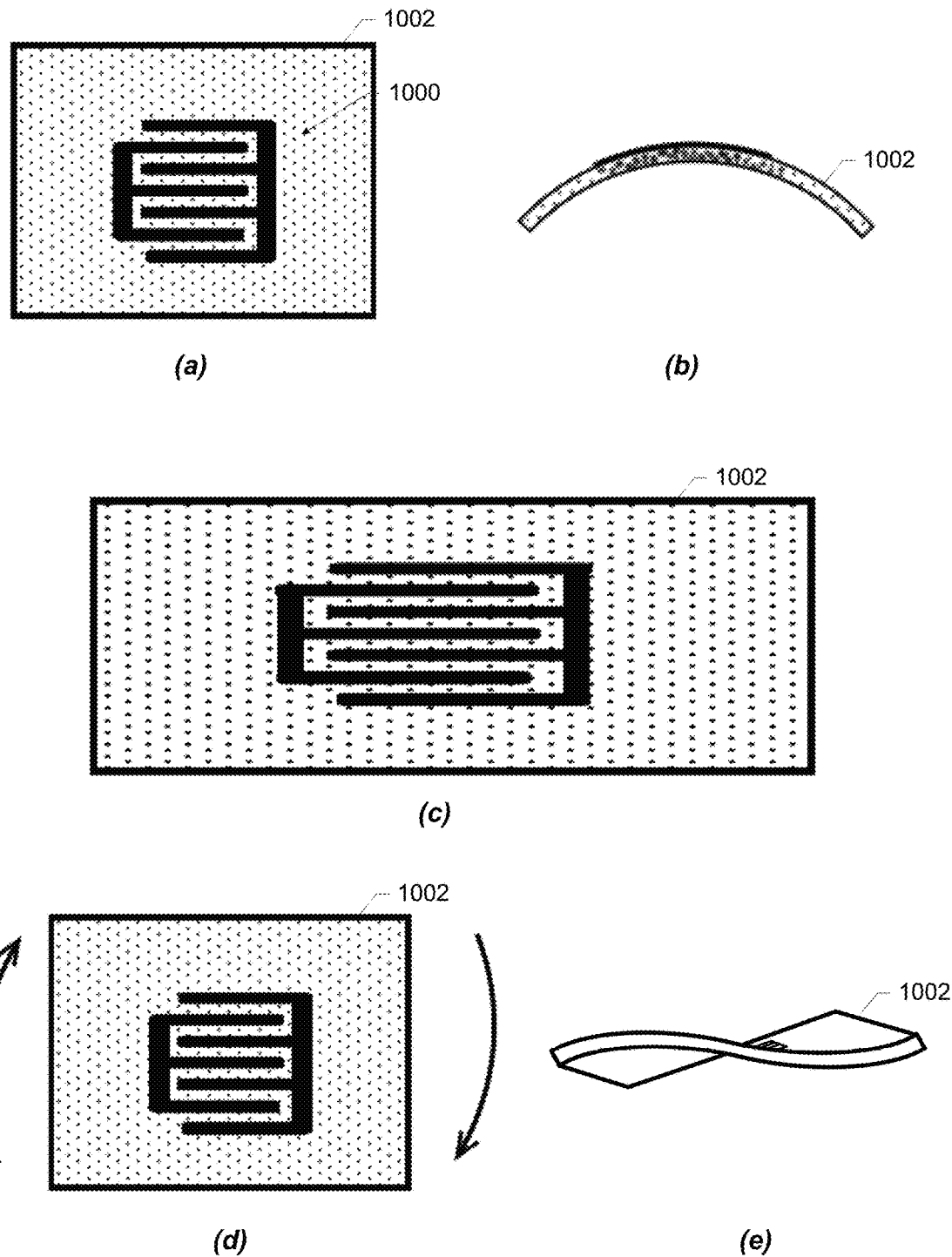
FIG. 11 shows examples of different types of distortions to a flexible substrate.

FIG. 11 shows examples of different types of distortions to flexible substrate 1002 that may be detected via sensor trace pattern 1000 (or any suitable trace pattern). FIG. 11(a) shows substrate 1002 in its non-distorted state. FIG. 11(b) shows a side view of substrate 1002 bending; FIG. 11(c) shows substrate 1002 stretching; FIG. 11(d) represents substrate 1002 rotating relative to surrounding material; and FIG. 11(e) shows a side view of substrate 1002 twisting due to an applied torque (i.e., torsion). In each of these scenarios, the resistance of the piezoresistive substrate changes in response to the applied force (e.g., goes down or up due to compression or increased separation of conductive particles in the substrate). This change (including its magnitude and time-varying nature) is detectable via sensor trace pattern 1000 and associated electronics (not shown).

Figure 12:
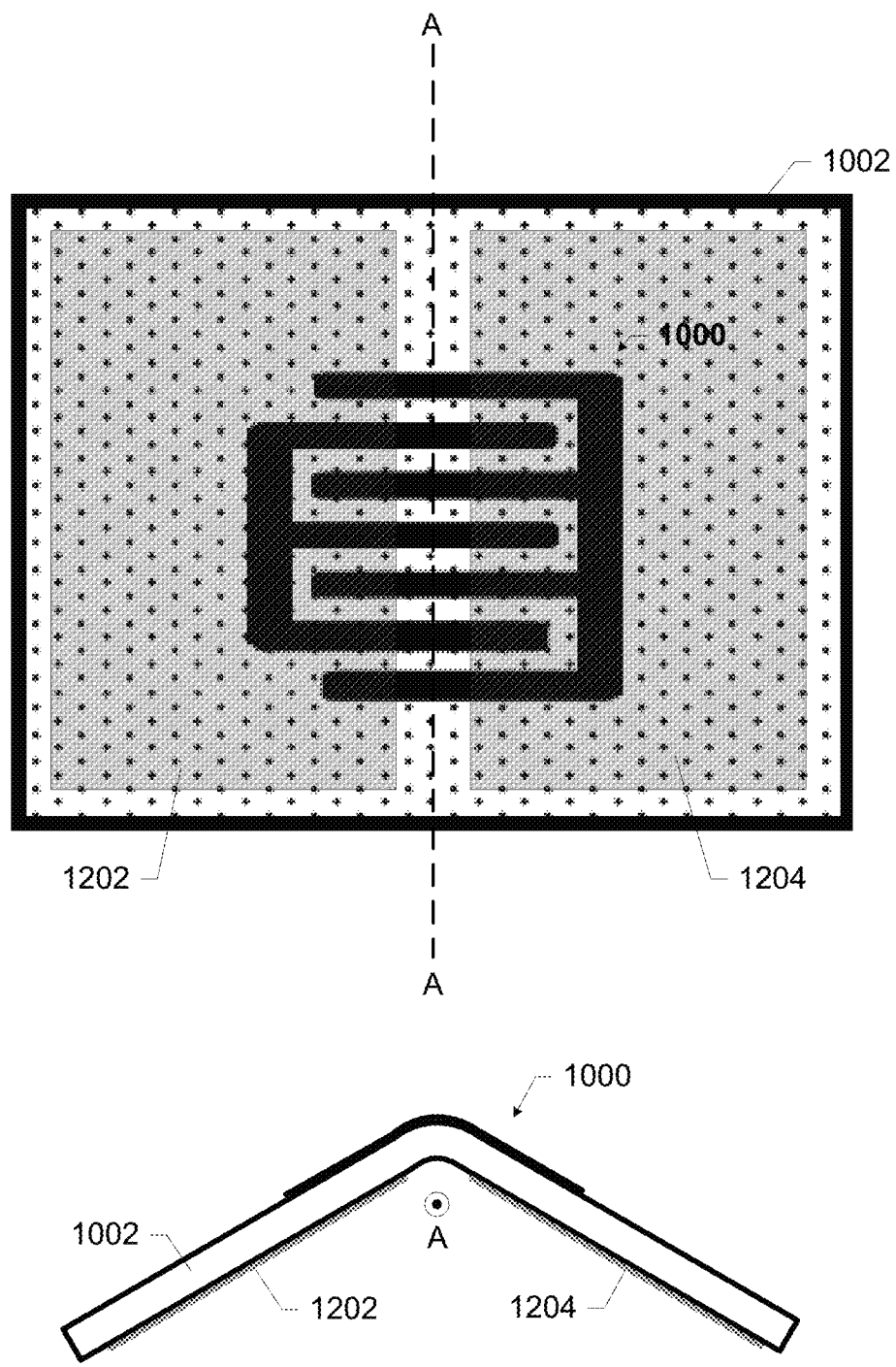
FIGS. 12 and 13 show examples of sensor configurations.

The response of a sensor designed as described herein may be manipulated to suit a wide variety of applications. For example, by constraining or restricting distortion and/or deformation of the flexible substrate in specific ways a sensor may be constructed to be selectively sensitive to particular types of force, distortion, etc. According to a particular class of implementations, specific areas of the flexible substrate with which the sensor traces are integrated are made stiffer than other areas of the substrate, thereby favoring particular types of distortions and/or deformations. This may be understood with reference to the example illustrated in FIG. 12 in which trace pattern 1000 coincides with stiffeners 1202 and 1204 that are also connected to or integrated with the flexible substrate 1002 with which the traces are integrated. In this example, stiffeners 1202 and 1204 promote bending of substrate 1002 along axis A-A; acting, effectively, like a flexible hinge as depicted in the side view. As will be appreciated the number, placement, and shape(s) of such stiffeners can be manipulated to favor or emphasize sensing of wide variety of distortions and/or deformations of the substrate.

Figure 13:
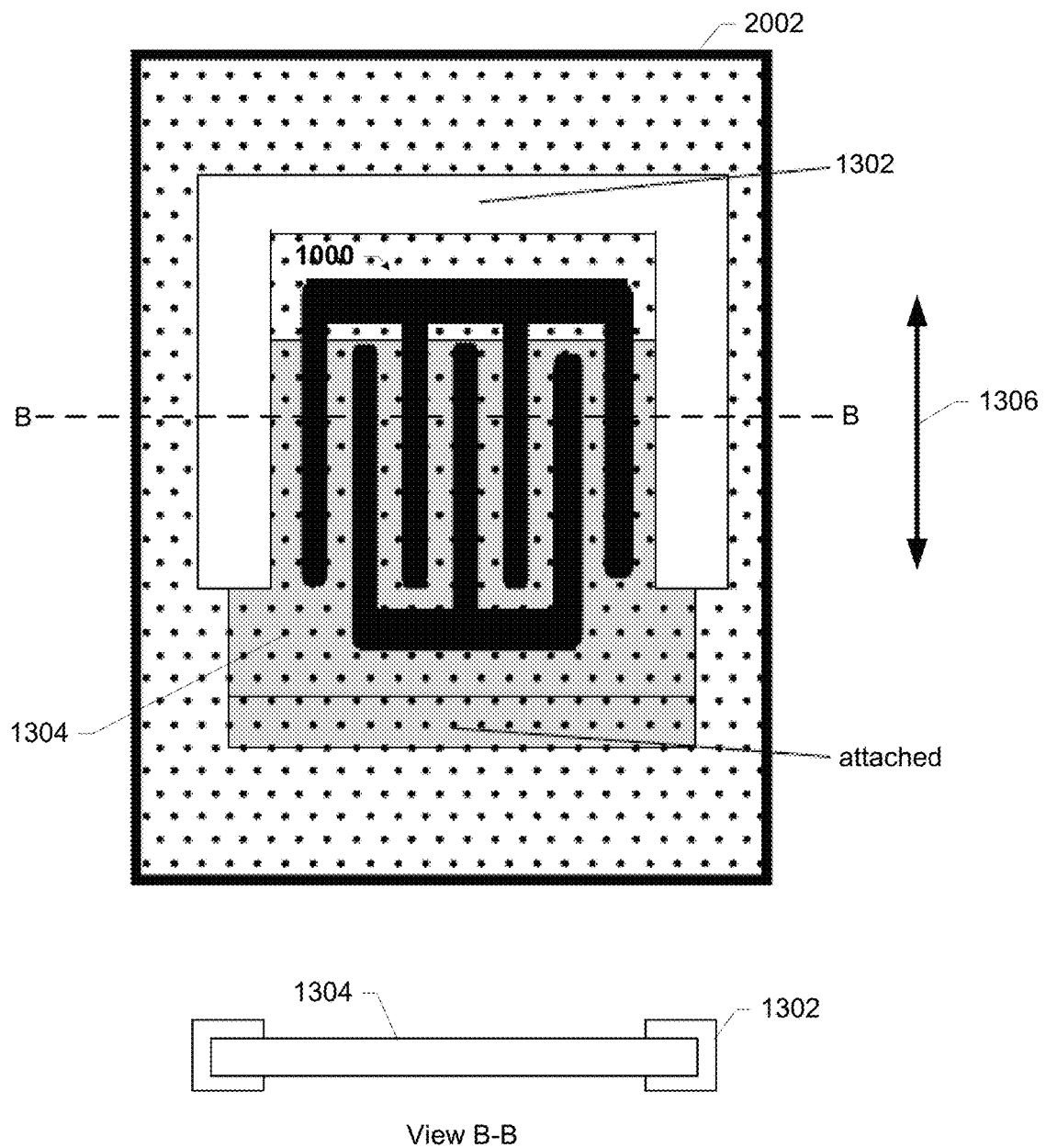

In another example illustrated in FIG. 13, a stretch sensor employs a channel stiffener 1302 and a slider stiffener 1304 that work together to promote distortion and/or deformation of substrate 1002 along axis 1306. Stiffener 1302 is formed around trace pattern 1000 and is attached to substrate 1002. As shown, portion of stiffener 1304 is attached to substrate 1002 while the remaining portion of stiffener 1304 is not attached to substrate 1002. The unattached portion of stiffener 1304 resides in a groove on the inside of stiffener 1302 as illustrated in View B-B. When substrate 1002 is stretched or compacted along axis 1306 the unattached portion of stiffener 1304 slides relative to stiffener 1302 thus promoting the distortions and/or deformation of substrate 1002 and the sensitivity of trace pattern 1000 to such forces. On the other hand, the stiffness of stiffeners 1302 and 1304 collectively reduce sensitivity to other types of forces, e.g., bends or twists of the substrate.

According to some implementations, a stiffener is an additional piece of material that is attached to the flexible substrate in the vicinity of the corresponding trace pattern. For example, the material may be a plastic film (e.g., polyethylene terephthalate or PET) attached to the flexible substrate in the vicinity of the trace pattern. Alternatively, the material may be another piece of fabric attached to the flexible substrate in the vicinity of the trace pattern. Such a fabric might be similar in thickness and density to the substrate, be thicker and/or denser than the substrate, or even be thinner and/or less dense than the substrate (i.e., with the combination of the substrate and the additional material still being stiffer than the substrate and trace pattern alone). As yet another alternative, a stiffening material such as, for example, DuPont 5036 Dielectric ink may be silk-screened or printed on the flexible substrate in the vicinity of the trace pattern.

In some implementations, stiffeners are attached to or formed on the flexible substrate on the opposite side of the substrate from the trace pattern. However, it should be noted that implementations are contemplated in which stiffeners are on the same side of the flexible substrate as the trace pattern, or even on both sides of the flexible substrate. For some implementations in which stiffeners are on the same side of the substrate as the trace pattern it may be preferable that the material of the stiffeners have little or no direct overlap with the traces so as not to reduce sensor response. Alternatively, implementations are contemplated in which stiffeners are intended to reduce the sensitivity of the sensor to forces that are not of interest. For example, a stiffener may cover all or portions of a trace pattern to reduce its sensitivity to a touch event in favor of the detection of forces that distort and/or deform the substrate.

Sensor response may also be manipulated through suitable choice of the materials from which the flexible substrate and/or the conductive traces are constructed. For example, the flexible substrate may be any of a variety of flexible materials (e.g., rubber, or a stretchable fabric such as spandex or open mesh fabrics) having piezoresistive properties.

While various specific implementations have been particularly shown and described, it will be understood by those skilled in the art that changes in the form and details of the disclosed implementations may be made without departing from the spirit or scope of this disclosure. In addition, although various advantages, aspects, and objects have been discussed herein with reference to various implementations, it will be understood that the scope of this disclosure should not be limited by reference to such advantages, aspects, and objects.

What is claimed is:

1. A sensor, comprising:
   piezoresistive fabric, the piezoresistive fabric having two opposing surfaces;
   a sensor trace pattern including two or more conductive traces of the sensor on a same one of the surfaces of the piezoresistive fabric, wherein resistance between the conductive traces varies with bending or stretching of the piezoresistive fabric;
   a plurality of stiffeners attached to or integrated with the piezoresistive fabric in a vicinity of the sensor trace pattern, the plurality of stiffeners including first and second stiffeners positioned relative to each other such that the piezoresistive fabric bends as a hinge along a particular axis in the vicinity of the sensor trace pattern, wherein the plurality of stiffeners are also configured to reduce sensitivity of the sensor to a particular type of force; and
   circuitry configured to receive one or more sensor signals from the conductive traces, and to generate one or more force signals representing the bending or stretching of the piezoresistive fabric based on the one or more sensor signals.

2. The sensor of claim 1, wherein the piezoresistive fabric is a stretchable piezoresistive material.

3. The sensor of claim 1, wherein the conductive traces comprise conductive ink printed on the piezoresistive fabric.

4. The sensor of claim 3, wherein the conductive ink comprises an elastomeric ink having conductive particles suspended therein.

5. The sensor of claim 1, wherein the conductive traces comprise conductive paint deposited on the piezoresistive fabric.

6. The sensor of claim 1, wherein the plurality of stiffeners include a plastic film, a fabric, or a cured stiffening agent.

7. The sensor of claim 1, wherein the plurality of stiffeners are configured such that the piezoresistive fabric stretches along a particular axis in a plane of the piezoresistive fabric in a region of the piezoresistive fabric in the vicinity of the sensor trace pattern.

8. The sensor of claim 1, further comprising circuitry configured to receive a first signal from the sensor trace pattern, and to generate a second signal based on the first signal, the second signal being representative of a magnitude and a time-varying characteristic of the bending or stretching of the piezoresistive fabric.

9. A sensor, comprising:
   piezoresistive fabric;
   a sensor trace pattern including two or more conductive traces of the sensor on the piezoresistive fabric, wherein resistance between the conductive traces varies with bending or stretching of the piezoresistive fabric; and
   a plurality of stiffeners attached to or integrated with the piezoresistive fabric in a vicinity of the sensor trace pattern, the plurality of stiffeners including first and second stiffeners, the first stiffener providing a channel in which the second stiffener slides along a particular axis parallel to a plane of the piezoresistive fabric.

10. The sensor of claim 9, wherein the piezoresistive fabric is a stretchable material.

11. The sensor of claim 9, wherein the plurality of stiffeners are further configured to reduce sensitivity of the sensor to a particular type of force.

12. The sensor of claim 9, wherein the plurality of stiffeners include a plastic film, a fabric, or a cured stiffening agent.

13. The sensor of claim 9, wherein the first and second stiffeners are configured such that the piezoresistive fabric stretches along the particular axis in a region of the piezoresistive fabric in the vicinity of the sensor trace pattern.

14. The sensor of claim 13, wherein the first and second stiffeners are further configured to resist distortion or deformation of the region of the piezoresistive fabric out of the plane of the piezoresistive fabric.

15. The sensor of claim 9, further comprising circuitry configured to receive a first signal from the sensor trace pattern, and to generate a second signal based on the first signal, the second signal being representative of a magnitude and a time-varying characteristic of the bending or stretching of the piezoresistive fabric.

16. The sensor of claim 9, wherein the conductive traces comprise conductive ink printed on the piezoresistive fabric.

17. The sensor of claim 16, wherein the conductive ink comprises an elastomeric ink having conductive particles suspended therein.

18. The sensor of claim 9, wherein the conductive traces comprise conductive paint deposited on the piezoresistive fabric.

19. The sensor of claim 9, further comprising circuitry configured to receive one or more sensor signals from the conductive traces, and to generate one or more force signals representing the bending or stretching of the piezoresistive fabric based on the one or more sensor signals.

* * * * *